(12) United States Patent
Fan et al.

(10) Patent No.: US 11,479,795 B2
(45) Date of Patent: Oct. 25, 2022

(54) GENETICALLY ENGINEERED BACTERIUM FOR SARCOSINE PRODUCTION AS WELL AS CONSTRUCTION METHOD AND APPLICATION

(71) Applicants: Tianjin University of Science and Technology, Tianjin (CN); Xintai Jiahe Biotech Co., Ltd., Tai'an (CN)

(72) Inventors: Xiaoguang Fan, Tianjin (CN); Yuhang Zhou, Tianjin (CN); Huajie Cao, Tai'an (CN); Pei Xie, Tai'an (CN); Jun Yang, Tai'an (CN); Junyu Tian, Tianjin (CN); Ning Chen, Tianjin (CN); Qingyang Xu, Tianjin (CN)

( * ) Notice: Subject to any disclaimer, the term of this patent is extended or adjusted under 35 U.S.C. 154(b) by 0 days.

(21) Appl. No.: 17/647,846

(22) Filed: Jan. 12, 2022

(65) Prior Publication Data

US 2022/0259625 A1    Aug. 18, 2022

Related U.S. Application Data

(63) Continuation of application No. PCT/CN2021/123534, filed on Oct. 13, 2021.

(51) Int. Cl.
| | |
|---|---|
| *C12P 13/00* | (2006.01) |
| *C12N 1/20* | (2006.01) |
| *C12N 9/88* | (2006.01) |
| *C12N 9/00* | (2006.01) |
| *C12N 9/06* | (2006.01) |
| *C12N 9/10* | (2006.01) |
| *C12N 9/02* | (2006.01) |
| *C12N 9/04* | (2006.01) |
| *C12N 9/12* | (2006.01) |
| *C12N 15/90* | (2006.01) |
| *C12R 1/19* | (2006.01) |

(52) U.S. Cl.
CPC ............ *C12P 13/001* (2013.01); *C12N 1/205* (2021.05); *C12N 9/0006* (2013.01); *C12N 9/0028* (2013.01); *C12N 9/0036* (2013.01); *C12N 9/1025* (2013.01); *C12N 9/1205* (2013.01); *C12N 9/88* (2013.01); *C12N 15/902* (2013.01); *C12Y 101/01081* (2013.01); *C12Y 101/01097* (2013.01); *C12Y 105/01021* (2013.01); *C12Y 106/01002* (2013.01); *C12Y 203/03001* (2013.01); *C12Y 203/03009* (2013.01); *C12Y 207/0104* (2013.01); *C12Y 401/01031* (2013.01); *C12Y 401/03001* (2013.01); *C12R 2001/19* (2021.05)

(58) Field of Classification Search
None
See application file for complete search history.

(56) References Cited

U.S. PATENT DOCUMENTS

2003/0119084 A1    6/2003  Shao et al.

FOREIGN PATENT DOCUMENTS

| CN | 103013941 A | 4/2013 |
|---|---|---|
| CN | 109957538 A | 7/2019 |
| CN | 110283798 A | 9/2019 |
| JP | H01168287 A | 7/1989 |
| JP | 4405324 B2 | 1/2010 |

OTHER PUBLICATIONS

Li ("Metabolic engineering of *Escherichia coli* using CRISPR-Cas9 mediated genome editing" Metabolic Engineering 31 (2015) 13-21). (Year: 2015).*
ATCC ("*Escherichia coli* (Migula) Castellani and Chalmers 27327" available at https://www.atcc.org/products/27325#detailed-product-information, Manassas, Virginia, accessed on Jul. 29, 2022) (Year: 2022).*
Bachmann ("Pedigree of Some Mutant Strains of *Eschericia coli* K-12" Bacteriological Reviews, 1972, 525-557) (Year: 1972).*
Blast, Ldh family oxidoreductase [Brevibacterium linens], Accession No. WP_101554530.1, «NCBI Genbank» , Feb. 2, 2018, Full text.
Tong Zhang et al., Production of L-theanine by recombinant *Escherichia coli* fermentation, «Food and Fermentation Industries» , vol. 45, No. 22, Sep. 5, 2019.
Lei Yang et al., Preparation and Characterization of Thermoresponsive Poly(N-Isopropylacrylamide) for Cell Culture Applications, «Polymers» , vol. 12, Feb. 9, 2020.
Yanjun Tong et al., Novel integration strategy coupling codon and fermentation optimization for efficiently enhancing sarcosine oxidase (SOX) production in recombinant *Escherichia coli*, «World J Microbiol Biotechnol» , vol. 31, Mar. 26, 2015.
Tuo Shi et al., Direct construction and fermentation optimization of valine producing strain, «Food and Fermentation Industries» , vol. 45, No. 5, Feb. 26, 2019.

* cited by examiner

*Primary Examiner* — Robert J Yamasaki
*Assistant Examiner* — Charles Zoltan Constantine

(57) ABSTRACT

The disclosure discloses a genetically engineered strain for sarcosine production as well as a construction method and application. The genetically engineered strain is obtained by using *Escherichia coli* as a host and by integrating a single copy of imine reductase gene dpkA on its genome; singly copying citrate synthase gene gltA; knocking out glyoxylate cycle inhibitor gene iclR; knocking out malate synthase gene aceB; integrating a single copy of isocitrate lyase gene aceA; integrating a single copy of membrane-bound transhydrogenase gene pntAB; knocking out 2-ketate reductase gene ycdW; integrating a single copy of phosphoenolpyruvate carboxylase gene ppc; and knocking out pyruvate kinase gene pykF. After system metabolism transformation, the engineered strain can synthesize sarcosine with glucose and methylamine as main raw materials. The sarcosine titer can reach 10 g/L after fermentation for 30 h in a 5 L fermenter.

3 Claims, 11 Drawing Sheets

Specification includes a Sequence Listing.

GENETICALLY ENGINEERED BACTERIUM FOR SARCOSINE PRODUCTION AS WELL AS CONSTRUCTION METHOD AND APPLICATION

CROSS REFERENCE TO RELATED APPLICATIONS

This application is a continuation of International Patent Application No. PCT/CN2021/123534 with a filing date of Oct. 13, 2021, designating the United States, now pending, and further claims priority to Chinese Patent Application No. 202110186880.6 with a filing date of Feb. 18, 2021. The content of the aforementioned applications, including any intervening amendments thereto, are incorporated herein by reference.

TECHNICAL FIELD

The disclosure relates to the technical field of gene engineering, particularly relates to a genetically engineered strain for sarcosine production as well as a construction method and application.

BACKGROUND OF THE DISCLOSURE

Sarcosine (N-methyl-L-glycine) is an N-methylated amino acid. Its sodium salt, sarcosine sodium, is often used as a precursor for the synthesis of some important products. Sarcosine is an important amino acid product which has considerable effect on the repair of brain and muscles damage. Meanwhile, sarcosine can provide quick-acting energy to the body, so as to alleviate the body fatigue. Sarcosine sodium and its downstream products are basically low-toxic, easy to degrade in nature and environmental-friendly. Thus, sarcosine has wide application prospects in the fields of aquaculture, food, health care and medicine.

Sarcosine is mainly obtained by the acidification of sarcosine sodium. The preparation method of sarcosine sodium is mainly chemical synthesis (CN201310676025.9 and CN200610155348.3), which has the disadvantages of harsh reaction conditions and difficult product separation.

Imine reductase DpkA (IRED) is an enzyme that can actively reduce imine bonds in cyclic and aliphatic compounds and can reduce piperidine-2-carboxylic acid into L-pipecolic acid. This reaction needs NADPH to provide a reducing force. Studies show that imine reductase DpkA can also catalyze the synthesis of sarcosine from glyoxylic acid and methylamine. Melanie Mindt et al. expressed imine reductase coding gene dpkA derived from *Pseudomonas putida* ATCC12633 in *Corynebacterium glutamicum* (Bioresource Technology, 2019:281, 135-142). The recombinant strain can use xylose and acetic acid as carbon sources and produce 8.7 g/L sarcosine through 126 h methylamine fed-batch fermentation.

Compared with *Corynebacterium glutamicum, Escherichia coli* has the advantages of simple culture conditions, short production cycle and low fermentation cost, and has a better industrial application value. To obtain a more high-yield production strains for sarcosine fermentation, this patent provides an efficient imine reductase which is derived from *Brevibacterium linens* ATCC9172 and has higher activity for sarcosine synthesis. Meanwhile, new metabolic engineering strategies are used to construct an engineered *Escherichia coli* for high-yield sarcosine production with glucose as carbon source.

To our knowledge, no patent publications related to the patent application of the disclosure have been found yet.

SUMMARY OF DISCLOSURE

The objective of the disclosure is to provide a genetically engineered strain for sarcosine production as well as a construction method and application, in order to overcome the shortcomings of the prior art.

The technical solution adopted by the disclosure to solve its technical problems is as follows:

Provided is a high-efficiency imine reductase which is derived from *Brevibacterium linens* ATCC9172, and its coding gene dpkA has a nucleotide sequence of SEQ ID NO:1.

Provided is a plasmid-free genetically engineered strain for efficiently sarcosine production by using cheap carbon source as the substrate. The genetically engineered strain is *Escherichia coli* SAR which is obtained by using *Escherichia coli* ATCC27325 as a host and through the following transformations: integrating a single copy of imine reductase gene dpkA, which is controlled by T7 promoter, on its genome; integrating a single copy of citrate synthase gene gltA, which is controlled by trc promoter, on its genome; knocking out glyoxylate cycle inhibitor gene iclR; knocking out malate synthase gene aceB; integrating a single copy of isocitrate lyase gene aceA, which is controlled by trc promoter, on its genome; integrating a single copy of membrane-bound transhydrogenase gene pntAB, which is controlled by trc promoter, on its genome; knocking out 2-ketate reductase gene ycdW; integrating a single copy of phosphoenolpyruvate carboxylase gene ppc, which is controlled by controlled by trc promoter, on its genome; and knocking out pyruvate kinase gene pykF.

Furthermore, the imine reductase gene dpkA is derived from *Brevibacterium linens* ATCC 9172, and has a nucleotide sequence of SEQ ID NO: 1.

Furthermore, the citrate synthase gene gltA is derived from *Escherichia coli* ATCC 27325, and has a nucleotide sequence of SEQ ID NO: 2.

Furthermore, the isocitrate lyase gene aceA is derived from *Escherichia coli* ATCC 27325, and has a nucleotide sequence of SEQ ID NO: 3.

Furthermore, the membrane-bound transhydrogenase gene pntAB is derived from *Escherichia coli* ATCC 27325, and has a nucleotide sequence of SEQ ID NO:4.

Furthermore, the phosphoenolpyruvate carboxylase gene ppc is derived from *Escherichia coli* ATCC 27325, and has a nucleotide sequence of SEQ ID NO:5.

Provided is a method for constructing a plasmid-free genetically engineered strain for efficiently sarcosine production by using cheap carbon source as the substrate, wherein the method uses a CRISPR/Cas9-mediated gene editing technology to perform targeted transformation on *Escherichia coli*, specifically comprising the following steps:

(1) in order to introduce the anabolism of sarcosine, imine reductase gene dpkA derived from *Brevibacterium linens* ATCC 9172 is singly copied at the mbhA site on *Escherichia coli* ATCC27325 genome, has a sequence of SEQ ID NO:1, is optimized by codons and is controlled by T7 promoter;

(2) in order to enhance the metabolism from oxaloacetate to citric acid, the endogenous citrate synthase gene gltA is singly copied at the ylbE site on the *Escherichia coli* ATCC27325 genome, has a sequence of SEQ ID NO:2, and is controlled by trc promoter;

(3) in order to perform glyoxylate cycle on strains under normal culture conditions, gene knockout is performed at the iclR site on *Escherichia coli* ATCC27325 genome;

(4) in order to block the metabolism from glyoxylic acid to malic acid, gene knockout is performed at the aceB site on *Escherichia coli* ATCC27325 genome;

(5) in order to enhance the metabolism from isocitrate to glyoxylic acid, endogenous isocitrate lyase gene aceA is singly copied at the yeeP site on *Escherichia coli* ATCC27325 genome, has a sequence of SEQ ID NO:3, and is controlled by trc promoter;

(6) in order to enhance the metabolism from NADH to NADPH, endogenous membrane-bound transhydrogenase gene pntAB was singly copied at the yghE site on *Escherichia coli* ATCC27325 genome, has a sequence of SEQ ID NO:4, and is controlled by trc promoter;

(7) in order to block the metabolism from glyoxylic acid to glycolic acid, gene knockout is performed at the ycdW site on *Escherichia coli* ATCC27325 genome;

(8) in order to enhance the metabolism from phosphoenolpyruvate to oxaloacetate, endogenous phosphoenolpyruvate carboxylase gene ppc is singly copied at the yeeL site on *Escherichia coli* ATCC27325 genome, has a sequence of SEQ ID NO:5, and is controlled by trc promoter;

(9) in order to reduce the metabolism from phosphoenolpyruvate to pyruvate, gene knockout is performed at the pykF site on *Escherichia coli* ATCC27325 genome;

wherein, the construction from steps (1) to (9) is in no order, and needs to be adjusted as required.

Provided is application of the above plasmid-free genetically engineered strain for efficiently sarcosine production by using cheap carbon source as the substrate.

Provided is a method for sarcosine fermentation using the above genetically engineered strain, specifically comprising the following steps:

Fermentation culture: the seed liquid of the genetically engineered strain is inoculated into a fresh fermentation culture medium in an inoculation volume of 15-20%. During the fermentation, pH is stably controlled at 6.8-7.2, and the temperature is maintained at 36.5-37.5° C. The dissolved oxygen is between 25% and 35%. When the glucose in the culture medium is completely consumed, 700-800 g/L glucose solution is fed for further culture and the concentration of glucose in the fermentation culture medium is maintained to be less than 3 g/L. When the $OD_{600}$ value is 40, 1.5-1.6 mol/L methylamine hydrochloride solution is fed at a flow rate of 20-25 mL/h with a feeding amount of 75 mL/L culture medium. The fermentation period is 28-32 h, and extracellular sarcosine is obtained.

The compositions of the fermentation culture medium: 15-25 g/L of glucose, 1-5 g/L of tryptone, 3-5 g/L of sodium citrate, 1-5 g/L of $KH_2PO_4$, 0.1-1 g/L of $MgSO_4.7H_2O$ and the balance of water, and pH 7.0-7.2.

The disclosure has the advantages and beneficial effects as follows:

1. The disclosure uses a high-efficiency imine reductase derived from *Brevibacterium linens* ATCC9172, and has higher activity forsarcosine synthesis.

2. There is no sarcosine anabolism pathway in *Escherichia coli*. To obtain strains capable of producing sarcosine through direct fermentation, the imine reductase gene derived from *Brevibacterium linens* ATCC9172 is integrated into a wild-type *Escherichia coli* genome, so that carbon metabolism can flow to the synthesis of sarcosine. In addition, the T7 promoter is used to regulate the expression of the imine reductase gene so as to enhance gene expression.

3. To increase the accumulation of precursor glyoxylic acid for sarcosine synthesis, the glyoxylate cycle inhibitor genes, the malate synthase genes and the 2-ketate reductase genes are knocked out, and the endogenous citrate synthase gene and the isocitrate lyase gene are introduced, so as to greatly increase the metabolic flow of pyruvate to precursor glyoxylic acid.

4. To increase the supply of NADPH required for reaction, the endogenous membrane-bound transhydrogenase genes are introduced, so that more intracellular NADH can be transformed into NADPH, thereby providing more reduction power required for sarcosine synthesis.

5. Through the system metabolic engineering strategies, it is realized for the first time that the genetically engineered *Escherichia coli* is constructed to synthesize sarcosine with glucose and methylamine as main raw materials. After fermentation for 30 h in a 5 L fermentor, the sarcosine titer can reach 10 g/L, which is the highest reported value at present. The constructed strain has good industrial application prospect.

6. The disclosure provides a plasmid-free genetically engineered strain for efficiently sarcosine production using cheap carbon source such as glucose as the substrate. The genetically engineered strain is obtained by using *Escherichia coli* as a host and by integrating single copy of imine reductase gene dpkA on its genome; integrating single copy of citrate synthase gene gltA; knocking out glyoxylate cycle inhibitor gene iclR; knocking out malate synthase gene aceB; integrating single copy of isocitrate lyase gene aceA; integrating single copy of membrane-bound transhydrogenase gene pntAB; knocking out 2-ketate reductase gene ycdW; integrating single copy of phosphoenolpyruvate carboxylase gene ppc; and knocking out pyruvate kinase gene pykF. Through system metabolism transformation, the engineered strain can use glucose and methylamine as main raw materials to synthesize sarcosine. After fermentation for 30 h in a 5 L fermentor, the sarcosine titer can reach 10 g/L.

DETAILED DESCRIPTION OF PREFERRED EMBODIMENTS

Figure 1:
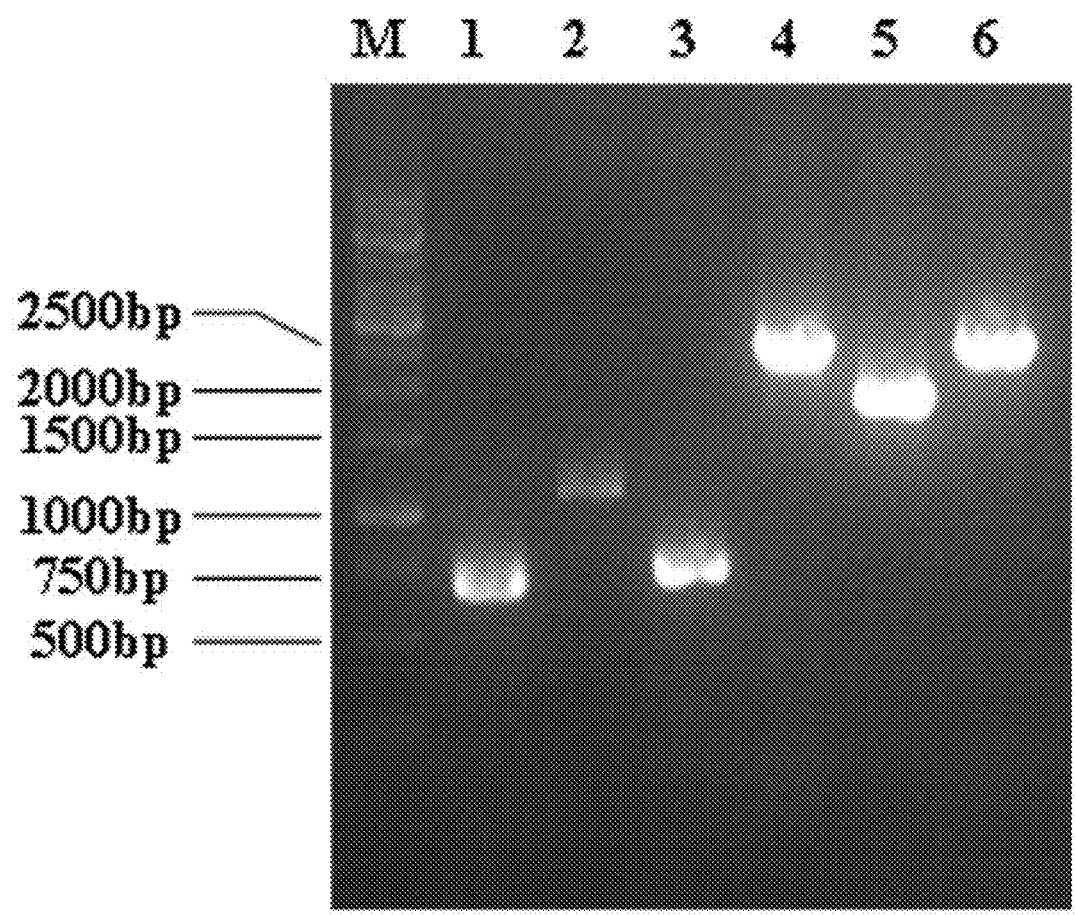
FIG. 1 is a mbhA::$P_{T7}$-dpkA integration electrophortogram in the disclosure; in which, M-1 kb Maker; 1-upstream homology arm; 2-target gene; 3-downstream homology arm; 4-overlapped fragments; 5-protobacterium PCR fragment; 6-PCR fragment of target strain.

Next, the disclosure will be further described in combination with embodiments. The following embodiments are narrative but not limiting, and cannot limit the protective scope of the disclosure based on the following embodiments.

The raw materials used in the disclosure, unless otherwise specified, are conventional commercial products. The methods used in the disclosure, unless otherwise specified, are conventional methods in the field, and the quality of each material used in the disclosure is conventionally used quality.

A new high-efficiency imine reductase is derived from *Brevibacterium linens* ATCC9172, and its coding gene dpkA has a nucleotide sequence of SEQ ID NO:1.

A plasmid-free genetically engineered bacterium for efficiently synthesizing Sarcosine by using a cheap carbon source as a substrate is *Escherichia coli* SAR, which is obtained by using *Escherichia coli* ATCC27325 as a host and through the following transformations: integrating singly copied imine reductase gene dpkA, which is controlled by T7 promoter, on its genome; singly copying citrate synthase gene gltA, which is controlled by trc promoter; knocking out glyoxylate cycle inhibitor gene iclR; knocking out malate synthase gene aceB; singly copying isocitrate lyase gene aceA, which is controlled by trc promoter; singly copying membrane-bound transhydrogenase gene pntAB, which is controlled by trc promoter; knocking out 2-ketate reductase gene ycdW; singly copying phosphoenolpyruvate carboxylase gene ppc, which is controlled by controlled by trc promoter; and knocking out pyruvate kinase gene pykF.

Preferably, the imine reductase gene dpkA is derived from *Brevibacterium linens* ATCC 9172, and has a nucleotide sequence of SEQ ID NO:1.

Preferably, the citrate synthase gene gltA is derived from *Escherichia coli* ATCC 27325, and has a nucleotide sequence of SEQ ID NO:2.

Preferably, the isocitrate lyase gene aceA is derived from *Escherichia coli* ATCC27325, and has a nucleotide sequence of SEQ ID NO:3.

Preferably, the membrane-bound transhydrogenase gene pntAB is derived from *Escherichia coli* ATCC27325, and has a nucleotide sequence of SEQ ID NO:4.

Preferably, the phosphoenolpyruvate carboxylase gene ppc is derived from *Escherichia coli* ATCC27325, and has a nucleotide sequence of SEQ ID NO:5.

Figure 11:
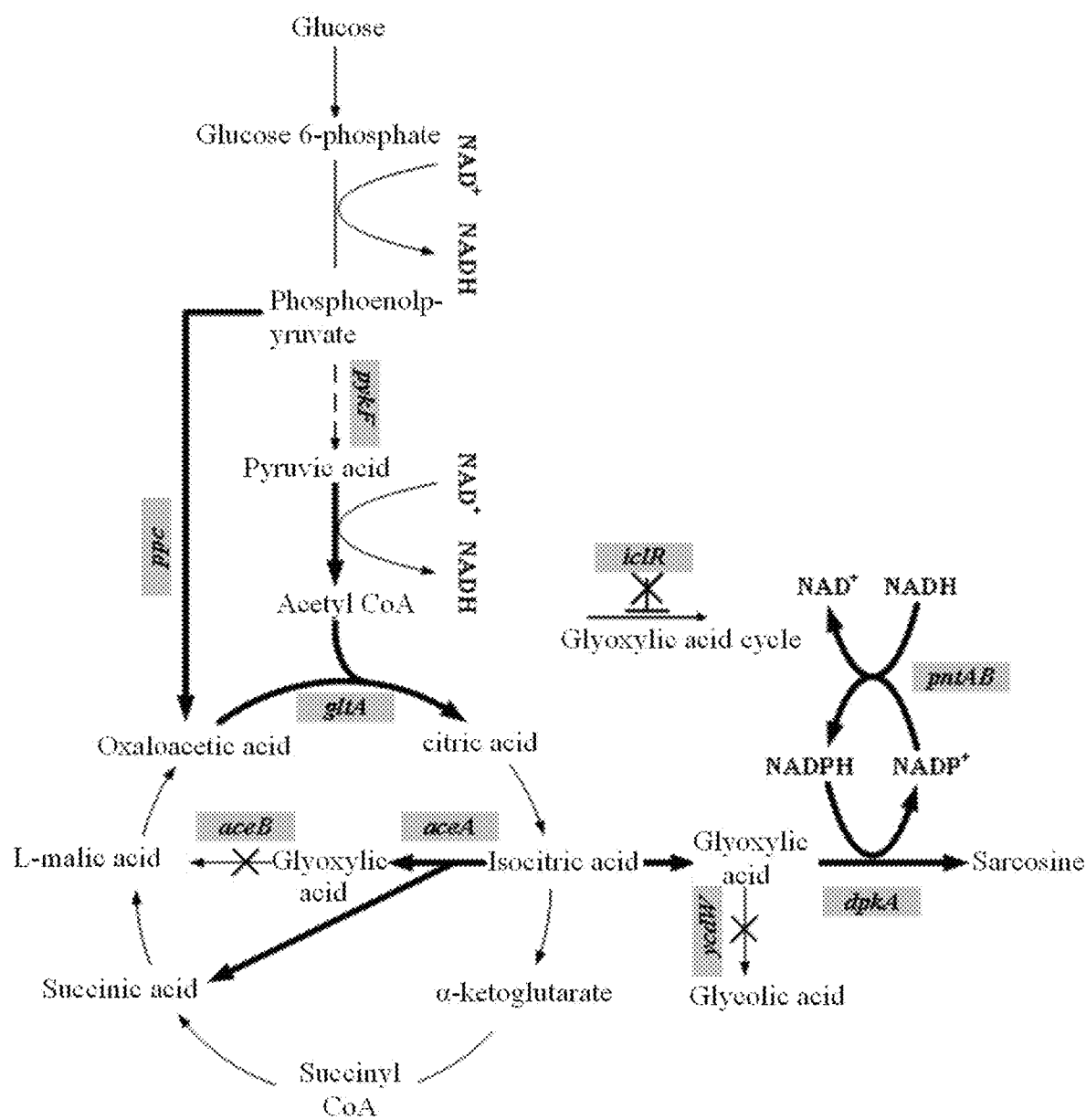
FIG. 11 shows an anabolism pathway of sarcosine constructed in *Escherichia coli* in the disclosure.

A method for constructing a genetically engineered bacterium for efficiently synthesizing Sarcosine by using a cheap carbon source as a substrate adopts a CRISPR/Cas9-mediated gene editing technology to perform targeted transformation on *Escherichia coli*, specifically comprising the following steps:

(1) in order to introduce the anabolism of Sarcosine, imine reductase gene dpkA derived from *Brevibacterium linens* ATCC 9172 is singly copied at the mbhA site on *Escherichia coli* ATCC27325 genome, has a sequence of SEQ ID NO:1, is optimized by codons and controlled by T7 promoter;

(2) in order to enhance the metabolism from oxaloacetate to citric acid, the endogenous citrate synthase gene gltA is singly copied at the ylbE site on *Escherichia coli* ATCC27325 genome, has a sequence of SEQ ID NO:2, and is controlled by trc promoter;

(3) in order to perform glyoxylate cycle on strains under normal culture conditions, gene knockout is performed at the iclR site on *Escherichia coli* ATCC27325 genome;

(4) in order to block the metabolism from glyoxylic acid to malic acid, gene knockout is performed at the aceB site on *Escherichia coli* ATCC27325 genome;

(4) in order to enhance the metabolism from isocitrate to glyoxylic acid, endogenous isocitrate lyase gene aceA is singly copied at the yeeP site on *Escherichia coli* ATCC27325 genome, has a sequence of SEQ ID NO:3 and is controlled by trc promoter;

(5) in order to enhance the metabolism from NADH to NADPH, endogenous membrane-bound transhydrogenase gene pntAB was singly copied at the yghE site on *Escherichia coli* ATCC27325 genome, has a sequence of SEQ ID NO:4 and is controlled by trc promoter;

(6) in order to block the metabolism from glyoxylic acid to glycolic acid, gene knockout is performed at the ycdW site on *Escherichia coli* ATCC27325 genome;

(7) in order to enhance the metabolism from phosphoenolpyruvate to oxaloacetate, endogenous phosphoenolpyruvate carboxylase gene ppc is singly copied at the yeeL site on *Escherichia coli* ATCC27325 genome, has a sequence of SEQ ID NO:5, and is controlled by trc promoter; and (8) in order to reduce the metabolism from phosphoenolpyruvate to pyruvate, gene knockout is performed at the pykF site on *Escherichia coli* ATCC27325 genome;

wherein, the construction from steps to is in no order, and needs to be adjusted as required, as shown in FIG. 11.

Provided is application of the above plasmid-free genetically engineered bacterium for efficiently synthesizing Sarcosine by using cheap a carbon source in production of Sarcosine.

A method for producing Sarcosine by fermenting the above genetically engineered bacterium specifically comprises the following steps:

Fermentation culture: the seed liquid of the genetically engineered bacteria is inoculated into a fresh fermentation culture medium in an inoculation volume of 15-20%; during the fermentation, pH is stably controlled at 6.8-7.2, the temperature is maintained at 36.5-37.5° C., and the dissolved oxygen is between 25% and 35%; when the glucose in the culture medium is completely consumed, 700-800 g/L glucose solution is fed for further culture and the concentration of glucose in the fermentation culture medium is maintained to be <3 g/L; when $OD_{600}$40, 1.5-1.6 mol/L methylamine hydrochloride solution is fed at a flow rate of 20-25 mL/h with a feeding amount of 75 mL/L culture medium, and a fermentation period is 28-32 h, so that Sarcosine is obtained;

the compositions of the fermentation culture medium: 15-25 g/L of glucose, 1-5 g/L of tryptone, 3-5 g/L of sodium citrate, 1-5 g/L of $KH_2PO_4$, 0.1-1 g/L of $MgSO_4.7H_2O$ and the balance of water, and pH 7.0-7.2.

Specifically, relevant preparation and detection examples are as follows:

Example 1: Construction of Genetically Engineered Strain *Escherichia coli* SAR 1. Gene Editing Method The disclosure adopted a CRISPR/Cas9-mediated gene editing method, which refers to a literature (Metabolic Engineering, 2015, 31:13-21). Two plasmids used in this method were pGRB and pREDCas9 respectively. The pREDCas9 contained a gRNA plasmid elimination system, a Red recombination system of λ phage and a Cas9 protein expression system. It had spectinomycin resistance (working concentration: 100 mg/L) and was cultured at 32° C. The pGRB plasmid used pUC18 as a backbone, including promoter J23100, a gRNA-Cas9 binding region sequence and a terminator sequence. It had ampicillin resistance (working concentration: 100 mg/L) and was cultured at 37° C.

2. Specific Process for Strain Construction 2.1 Integration of $P_{T7}$-dpkA (a Fragment Containing dpkA Gene and T7 Promoter) at the mbhA Site An *E. coli* ATCC27325 genome was used as a template. Upstream homology arm primers UP-mbhA-S(SEQ ID NO:6) and UP-mbhA-A (SEQ ID NO:7) and downstream homology arm primers DN-mbhA-S(SEQ ID NO:8) and DN-mbhA-A (SEQ ID NO:9) were designed according to upstream and downstream sequences of its mbhA gene. The upstream and downstream homology arm fragments were subjected to PCR amplification. Primers dpkA-S(SEQ ID NO:10) and dpkA-A (SEQ ID NO:11) were designed according to the dpkA gene, and the dpkA gene fragment (SEQ ID NO:1) was amplified. Promoter $P_{T7}$ was designed in the downstream primer of the upstream homology arm and the upstream primer of the dpkA gene. The integrated fragment (mbhA gene upstream homology arm-$P_{T7}$-dpkA-mbhA-gene downstream homology arm) of the dpkA gene was obtained by overlapping PCR of the above fragments. A DNA fragment which was used for constructing the pGRB-mbhA and contained a target sequence was obtained by annealing primers gRNA-mbhA-S(SEQ ID NO:12) and gRNA-mbhA-A (SEQ ID NO:13). The DNA fragment was recombined with a linearized pGRB vector to obtain recombinant pGRB-mbhA. The integrated fragment and pGRB-mbhA were electro transformed into *E. coli* ATCC27325 competent cells containing pREDCas9. The resuscitated strains after electrotransformation were coated on an LB plate containing ampicillin and spectinomycin and cultured overnight at 32° C., and the positive recons were verified via PCR. Subsequently, pGRB-mbhA used for gene editing was eliminated, so as to finally obtain strain *E. coli* SAR7.

In the integration process of the $P_{T7}$-dpkA fragment, an electrophortogram for the construction of the integrated fragment and the PCR verification of the positive strains is shown in FIG. 1. Wherein, the length of the upstream homology arm is 682 bp, the length of the dpkA gene fragment is 1006 bp, the length of the downstream homology arm is 720 bp, and the length of the overlapped fragment is 2457 bp. When the recons are verified via PCR, the length of the fragment amplified by the positive recons is 2457 bp, and the length of the fragment amplified by protobacteria is 1837 bp.

2.2 Integration of $P_{trc}$-gltA (a Fragment Containing gltA Gene and Trc Promoter) at the Site ylbE An *E. coli* ATCC27325 genome was used as a template. Upstream homology arm primers UP-ylbE-S(SEQ ID NO:14) and UP-ylbE-A (SEQ ID NO:15) and downstream homology arm primers DN-ylbE-S(SEQ ID NO:16) and DN-ylbE-A (SEQ ID NO:17) were designed according to upstream and downstream sequences of its ylbE gene. The upstream and downstream homology arms of the ylbE gene were amplified. Primers gltA-S(SEQ ID NO:18) and gltA-A (SEQ ID NO:19) were designed according to the gltA gene, and the gltA gene fragment (SEQ ID NO:2) was amplified. Promoter $P_{trc}$ was designed in the downstream primer of the upstream homology arm of the ylbE gene and the upstream primer of the gltA gene. The integrated fragment (ylbE gene upstream homology arm-$P_{trc}$-gltA-ylbE-gene downstream homology arm) of the gltA gene was obtained by overlapping PCR of the above fragments. A DNA fragment which was used for constructing the pGRB-ylbE and contained a target sequence was obtained by annealing primers gRNA-ylbE-S(SEQ ID NO:20) and gRNA-ylbE-A (SEQ ID NO:21). The DNA fragment was recombined with a linearized pGRB vector to obtain recombinant pGRB-ylbE. The integrated fragment and pGRB-ylbE were electro transformed into *E. coli* SAR7 competent cells containing a pREDCas9 vector. The resuscitated strains after electrotransformation were coated on an LB plate containing ampicillin and spectinomycin and cultured overnight at 32° C., and the positive recons were verified via PCR. Subsequently pGRB-ylbE and pREDCas9 used for gene editing were eliminated, so as to finally obtain strain *E. coli* SAR2.

Figure 2:
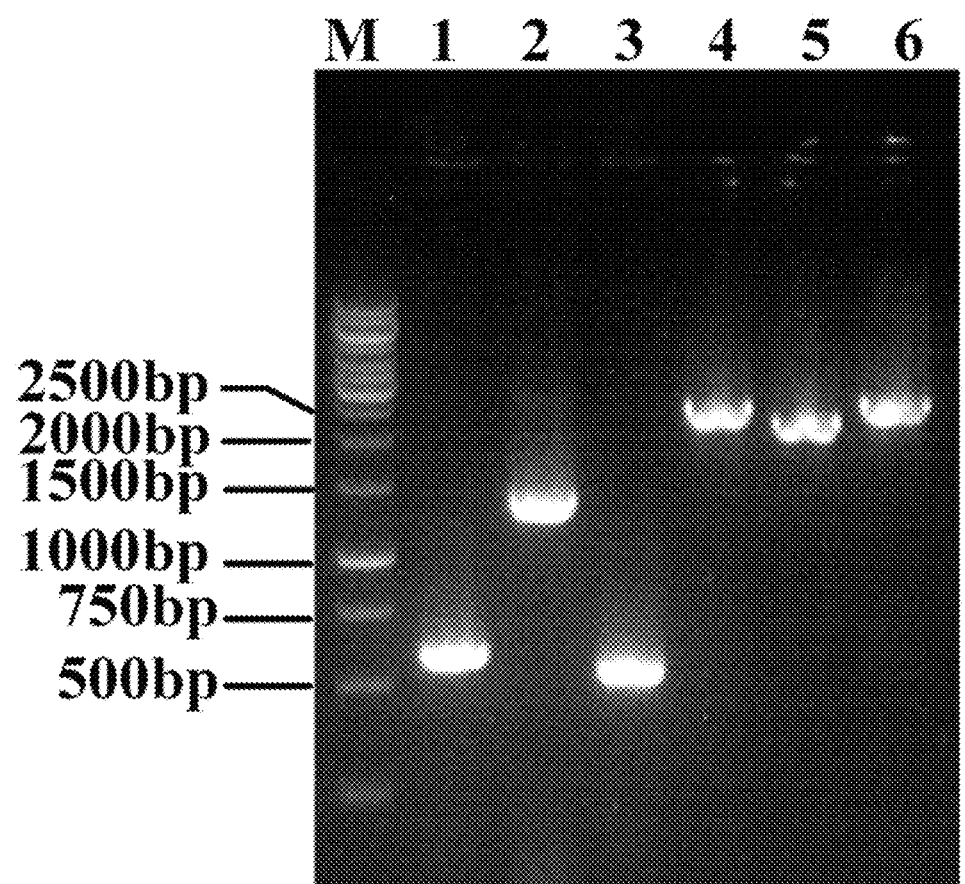
FIG. 2 is a ylbE::$P_{trc}$-gltA integration electrophortogram in the disclosure; in which, M-1 kb Maker; 1-upstream homology arm; 2-target gene; 3-downstream homology arm; 4-overlapped fragment; 5-protobacterium PCR fragment; 6-PCR fragment of target strain.

An electrophortogram for the construction of the $P_{trc}$-gltA integrated fragment and the PCR verification of the positive strains is shown in FIG. 2. Wherein, the length of the upstream homology arm is 601 bp, the length of the gltA gene fragment is 1407 bp, the length of the downstream homology arm is 547 bp, and the total length of the integrated fragment is 2474 bp. When PCR verification is carried out, the length of the fragment subjected to PCR amplification by positive bacteria is 2474 bp, and the length of the fragment amplified by protobacteria is 2184 bp.

2.3 Knockout of iclR Gene

An *E. coli* ATCC27325 genome was used as a template. Upstream homology arm primers UP-iclR-S(SEQ ID NO:22) and UP-iclR-A (SEQ ID NO:23) and downstream homology arm primers DN-iclR-S(SEQ ID NO:24) and DN-iclR-A (SEQ ID NO:25) were designed according to upstream and downstream sequences of its iclR gene. The upstream and downstream homology arms of the iclR gene were amplified. The iclR gene knockout fragment (iclR gene upstream homology arm-iclR gene downstream homology arm) was obtained by overlapping PCR of the above fragments. A DNA fragment which was used for constructing the pGRB-iclR and contained a target sequence was obtained by annealing primers gRNA-iclR-S(SEQ ID NO:26) and gRNA-iclR-A (SEQ ID NO:27). The DNA fragment was recombined with a linearized pGRB vector to obtain recombinant pGRB-iclR. The integrated fragment and pGRB-iclR were electrotransformed into *E. coli* SAR2 competent cells containing a pREDCas9 vector. The resuscitated strains after electrotransformation were coated on an LB plate containing ampicillin and spectinomycin and cultured overnight at 32°

C., and the positive recons were verified via PCR. Subsequently pGRB-iclR and pREDCas9 used for gene editing were eliminated, so as to finally obtain strain *E. coli* SAR3.

Figure 3:
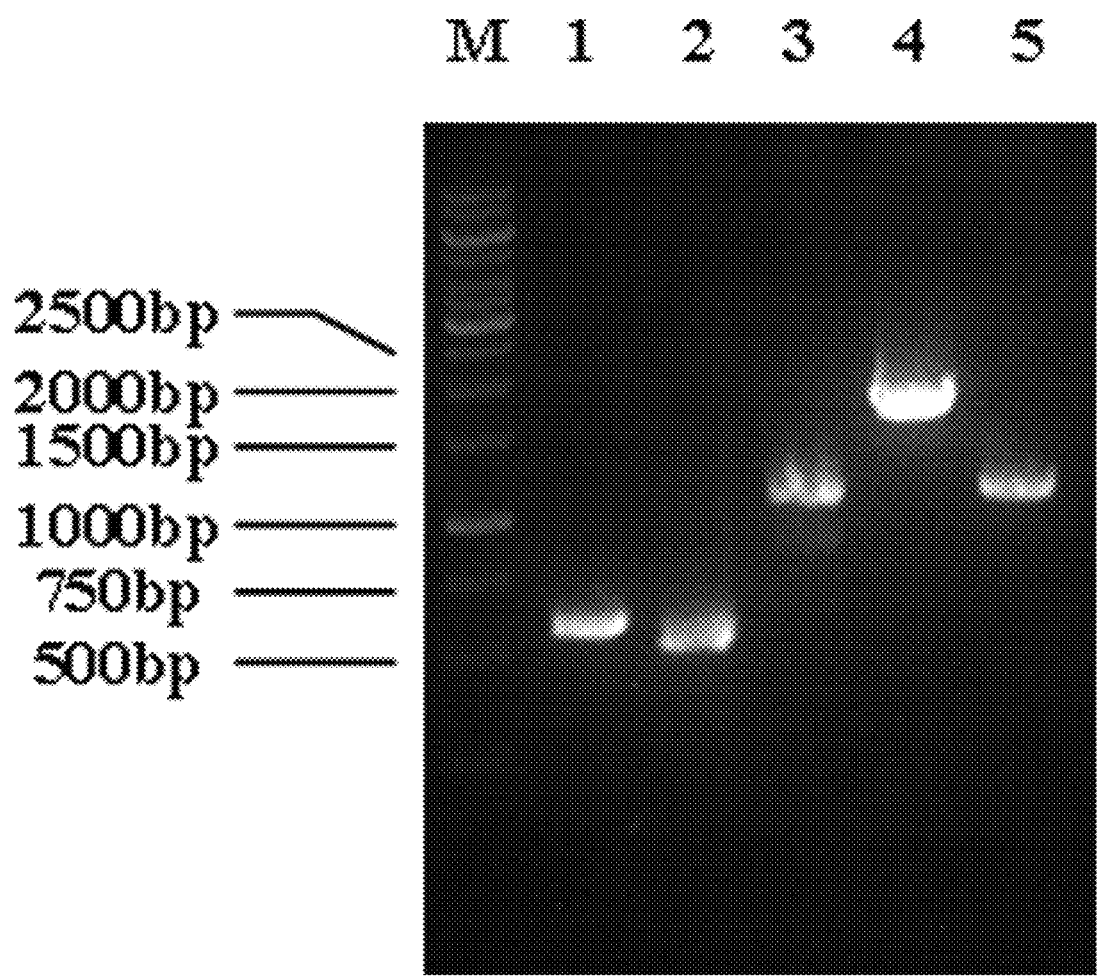
FIG. 3 is an iclR knockout electrophortogram in the disclosure; in which, M-1 kb Maker; 1-upstream homology arm; 2-downstream homology arm; 3-overlapped fragment; 4-protobacterium PCR fragment; 5-PCR fragment of target strain.

An electrophortogram for the construction of the iclR gene knockout fragment and the PCR verification of the positive strains is shown in FIG. 3. Wherein, the length of the upstream homology arm is 595 bp, the length of the downstream homology arm is 532 bp, the total length of the gene knockout fragment is 1086 bp. When PCR verification is carried out, the length of the fragment subjected to PCR amplification by positive bacteria is 1086 bp, and the length of the fragment subjected to PCR amplification by protobacteria is 1745 bp.

2.4 Knockout of aceB Gene

An *E. coli* ATCC27325 genome was used as a template. Upstream homology arm primers UP-aceB-S(SEQ ID NO:28) and UP-aceB-A (SEQ ID NO:29) and downstream homology arm primers DN-aceB-S(SEQ ID NO:30) and DN-aceB-A (SEQ ID NO:31) were designed according to upstream and downstream sequences of its aceB gene. The upstream and downstream homology arms of the aceB gene were amplified. The aceB gene knockout fragment (aceB gene upstream homology arm-aceB gene downstream homology arm) was obtained by overlapping PCR of the above fragments, A DNA fragment which was used for constructing the pGRB-aceB and contained a target sequence was obtained by annealing primers gRNA-aceB-S(SEQ ID NO:32) and gRNA-aceB-A (SEQ ID NO:33). The DNA fragment was recombined with a linearized pGRB vector to obtain recombinant pGRB-aceB. The integrated fragment and pGRB-iclR were electrotransformed into *E. coli* SAR3 competent cells containing a pREDCas9 vector. The resuscitated strains after electrotransformation were coated on an LB plate containing ampicillin and spectinomycin and cultured overnight at 32° C., and the positive recons were verified via PCR. Subsequently pGRB-iclR and pREDCas9 used for gene editing were eliminated, so as to finally obtain strain *E. coli* SAR4.

Figure 4:
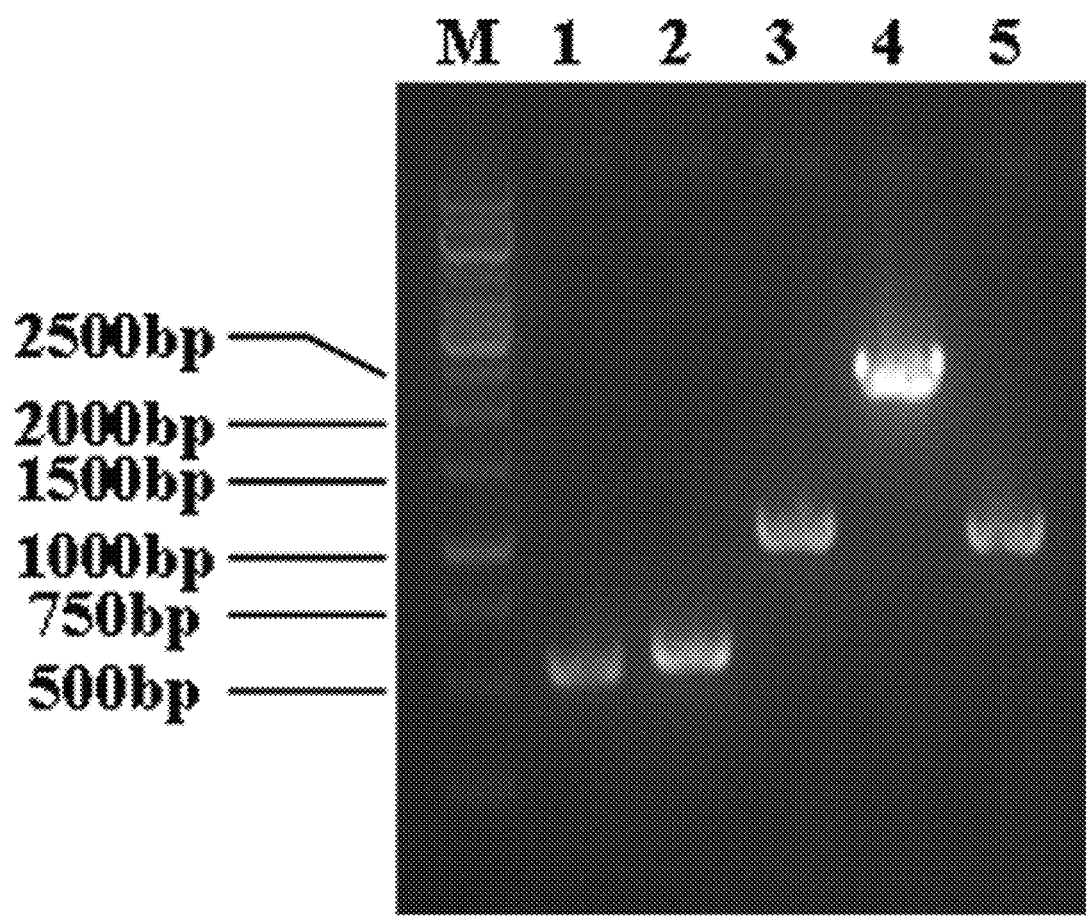
FIG. 4 is an aceB knockout electrophortogram in the disclosure; in which, M-1 kb Maker; 1-upstream homology arm; 2-downstream homology arm; 3-overlapped fragment; 4-protobacterium PCR fragments; 5-PCR fragment of target strain.

An electrophortogram for the construction of the aceB gene knockout fragment and the PCR verification of the positive strains is shown in FIG. 4. Wherein, the length of the upstream homology arm is 538 bp, the length of the downstream homology arm is 586 bp, the total length of the gene knockout fragment is 1082 bp. When PCR verification is carried out, the length of the fragment amplified by positive bacteria is 1082 bp, and the length of the fragment subjected to PCR amplification by protobacteria is 2397 bp.

2.5 Integration of $P_{trc}$-aceA (a Fragment Containing aceA Gene and Trc Promoter) at the Site yeeP An *E. coli* ATCC27325 genome was used as a template. Upstream homology arm primers UP-yeeP-S(SEQ ID NO.34) and UP-yeeP-A (SEQ ID NO.35) and downstream homology arm primers DN-yeeP-S(SEQ ID NO.36) and DN-yeeP-A (SEQ ID NO.37) were designed according to upstream and downstream sequences of its yeeP gene. The upstream and downstream homology arms of the yeeP gene were amplified. Primers aceA-S(SEQ ID NO.38) and aceA-A (SEQ ID NO.39) were designed according to the aceA gene, and the aceA gene fragment (SEQ ID. NO: 3) was amplified. Promoter $P_{trc}$ was designed in the downstream primer of the yeeP gene upstream homology arm and the upstream primer of the aceA gene. The integrated fragment (yeeP gene upstream homology arm-$P_{trc}$-aceA-yeeP gene downstream homology arm) of the aceA gene was obtained by overlapping PCR of the above fragments. A DNA fragment which was used for constructing pGRB-yeeP and contained a target sequence was obtained by annealing primers gRNA-yeeP-S(SEQ ID NO: 40) and gRNA-yeeP-A (SEQ ID NO: 41). The DNA fragment was recombined with a linearized pGRB vector to obtain recombinant pGRB-yeeP. The integrated fragment and pGRB-yeeP were electrotransformed into *E. coli* SAR4 competent cells containing a pREDCas9 vector. The resuscitated strains after electrotransformation were coated on an LB plate containing ampicillin and spectinomycin and cultured overnight at 32° C., and the positive recons were verified via PCR. Subsequently pGRB-yeeP and pREDCas9 used for gene editing were eliminated, so as to finally obtain strain *E. coli* SAR5.

Figure 5:
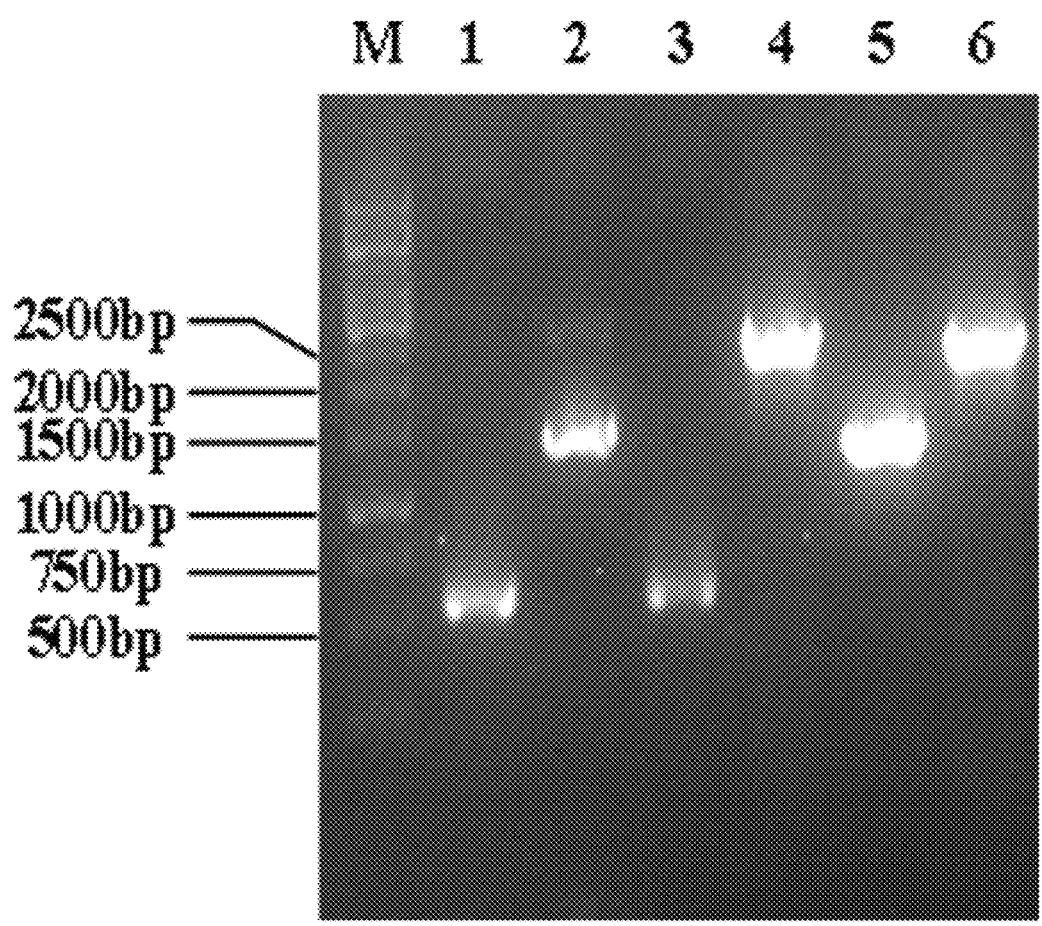
FIG. 5 is a yeeP::Ptrc-aceA integration electrophortogram in the disclosure; in which, M-1 kb Maker; 1-upstream homology arm; 2-target gene; 3-downstream homology arm; 4-overlapped fragment; 5-protobacterium PCR fragment; 6-PCR fragment of target strain.

An electrophortogram for the construction of the $P_{trc}$-aceA integrated fragment and the PCR verification of the positive strain is shown in FIG. 5. Wherein, the length of the upstream homology arm is 568 bp, the length of the aceA gene fragment is 1428 bp, the length of the downstream homology arm is 576 bp, the total length of the integrated fragment is 2491 bp. When in PCR verification, the length of the fragment subjected to PCR amplification by positive bacteria is 2491 bp, and the length of the fragment subjected to PCR amplification by protobacteria is 1396 bp.

2.6 Integration of $P_{trc}$-pntAB (a Fragment Containing pntAB Gene and Trc Promoter) at the Site yghE An *E. coli* ATCC27325 genome was used as a template. Upstream homology arm primers UP-yghE-S(SEQ ID NO:42) and UP-yghE-A (SEQ ID NO:43) and downstream homology arm primers DN-yghE-S(SEQ ID NO.44) and DN-yghE-A (SEQ ID NO.45) were designed according to upstream and downstream sequences of its yghE gene. The upstream and downstream homology arms of the yghE gene were amplified. Primers pntAB-S(SEQ ID NO.46) and pntAB-A (SEQ ID NO.47) were designed according to the pntAB gene, and the pntAB gene fragment (SEQ ID. NO: 3) was amplified. Promoter $P_{trc}$ was designed in the downstream primer of the yghE gene upstream homology arm and the upstream primer of the pntAB gene. The integrated fragment (yghE gene upstream homology arm-$P_{trc}$-pntAB-yghE gene downstream homology arm) was obtained by overlapping PCR of the above fragments. A DNA fragment which was used for constructing pGRB-yghE and contained a target sequence was obtained by annealing primers gRNA-yghE-S(SEQ ID NO: 48) and gRNA-yghE-A (SEQ ID NO:49). The DNA fragment was recombined with a linearized pGRB vector to obtain recombinant pGRB-yghE. The integrated fragment and pGRB-yghE were electrotransformed into *E. coli* SAR5 competent cells containing a pREDCas9 vector. The resuscitated strains after electrotransformation were coated on an LB plate containing ampicillin and spectinomycin and cultured overnight at 32° C., and the positive recons were verified via PCR. Subsequently pGRB-yghE and pREDCas9 used for gene editing were eliminated, so as to finally obtain strain *E. coli* SAR6.

Figure 6:
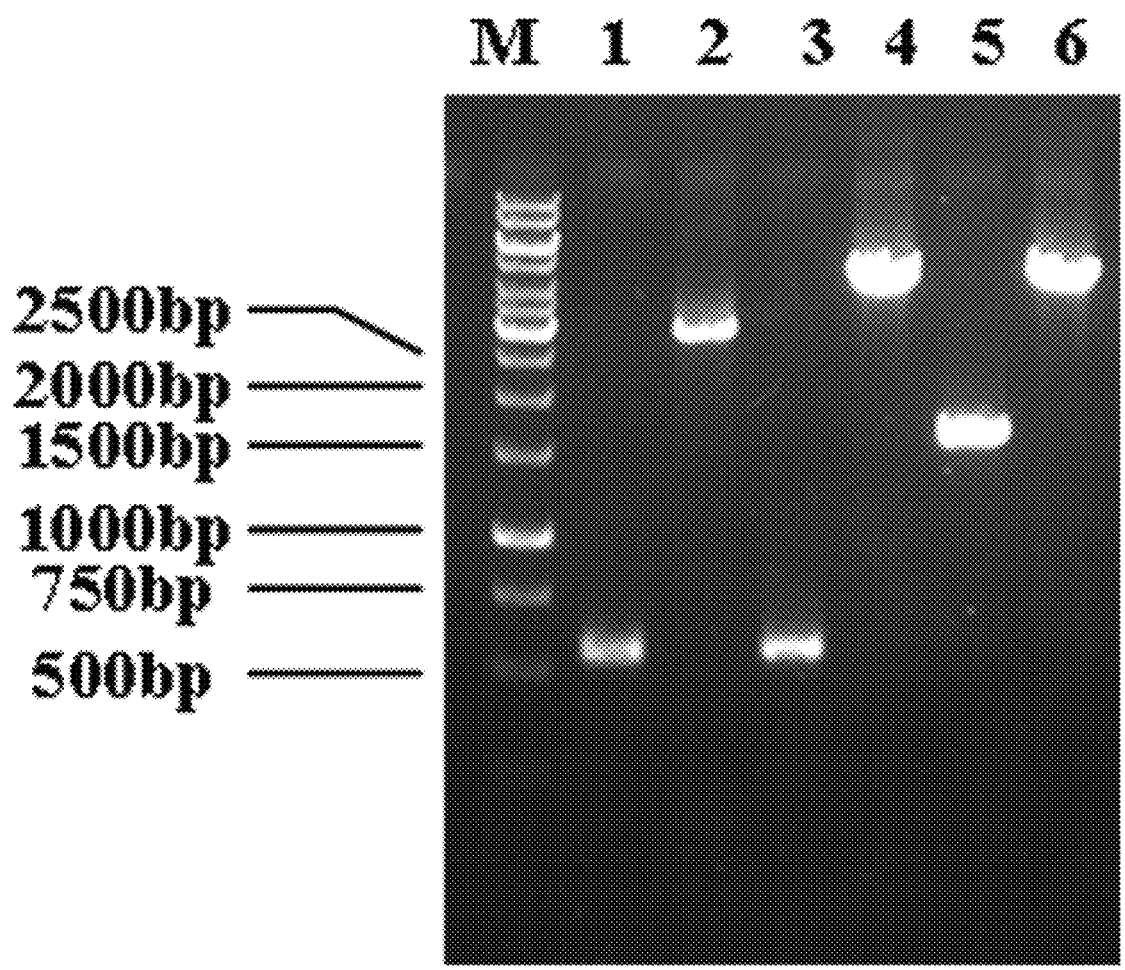
FIG. 6 is a yghE::$P_{trc}$-pntAB integration electrophortogram in the disclosure; in which, M-1 kb Maker; 1-upstream homology arm; 2-target gene; 3-downstream homology arm; 4-overlapped fragment; 5-protobacterium PCR fragment; 6-PCR fragment of target strain.

The electrophortogram of the construction of the $P_{trc}$-pntAB integrated fragment and the PCR verification of the positive strains was as shown in FIG. 6. Wherein, the length of the upstream homology arm is 559 bp, the length of the pntAB gene fragment is 3050 bp, the length of the downstream homology arm is 549 bp, and the total length of the integrated fragment is 4087 bp. When in PCR verification, the length of the fragment subjected to PCR amplification by positive bacteria is 4087 bp, and the length of the fragment subjected to PCR amplification by protobacteria is 1547 bp.

2.7 Knockout of ycdW Gene

An *E. coli* ATCC27325 genome was used as a template. Upstream homology arm primers UP-ycdW-S(SEQ ID NO.50) and UP-ycdW-A (SEQ ID NO.51) and downstream homology arm primers DN-ycdW-S(SEQ ID NO:52) and DN-ycdW-A (SEQ ID NO:53) were designed according to upstream and downstream sequences of its ycdW gene. The upstream and downstream homology arms of the ycdW gene were amplified. The ycdW gene knockout fragment (ycdW gene upstream homology arm-ycdW gene downstream homology arm) was obtained by overlapping PCR. A DNA fragment which was used for constructing pGRB-ycdW and contained a target sequence was obtained by annealing primers gRNA-ycdW-S(SEQ ID NO:54) and gRNA-ycdW-A (SEQ ID NO:55). The DNA fragment was recombined with a linearized pGRB vector to obtain recombinant pGRB-ycdW. The integrated fragment and pGRB-ycdW were electrotransformed into E. coli SAR6 competent cells containing a pREDCas9 vector. The resuscitated strains after electrotransformation were coated on an LB plate containing ampicillin and spectinomycin and cultured overnight at 32° C., and the positive recons were verified via PCR. Subsequently pGRB-ycdW and pREDCas9 used for gene editing were eliminated, so as to finally obtain strain E. coli SAR7.

Figure 7:
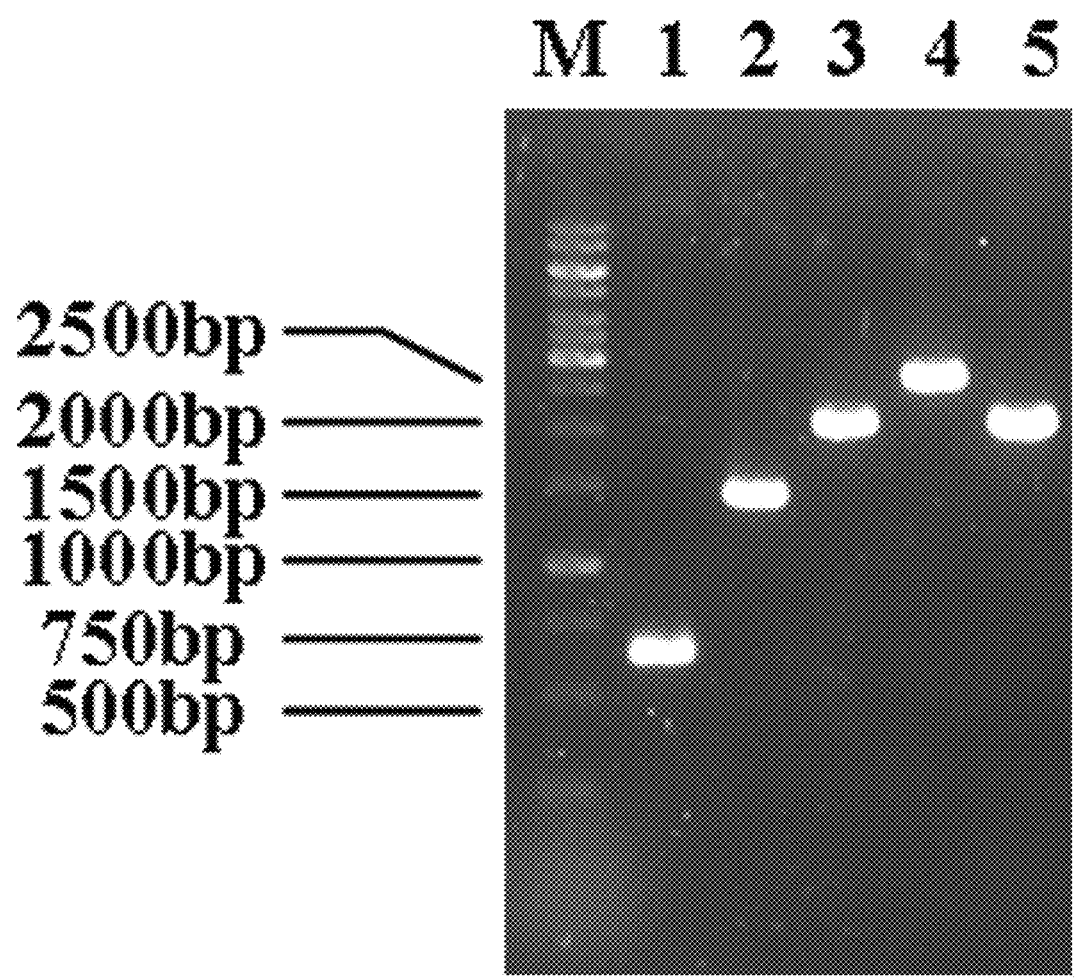
FIG. 7 is an ycdW knockout electrophortogram in the disclosure; in which, M-1 kb Maker; 1-upstream homology arm; 2-downstream homology arm; 3-overlapped fragment; 4-protobacterium PCR fragment; 5-PCR fragment of target strain.

The electrophortogram of the construction of the ycdW gene knockout fragment and the PCR verification of the positive strains is as shown in FIG. 7. Wherein, the length of the upstream homology arm is 642 bp, the length of the downstream homology arm is 1428 bp, the total length of the gene knockout fragment is 2024 bp. When in PCR verification, the length of the fragment subjected to PCR amplification by positive bacteria is 2024 bp, and the length of the fragment subjected to PCR amplification by protobacteria is 2604 bp.

2.8 Integration of $P_{trc}$-Ppc (a Fragment Containing Ppc Gene and Trc Promoter) at the Site yeeL An E. coli ATCC27325 genome was used as a template. Upstream homology arm primers UP-yeeL-S(SEQ ID NO:56) and UP-yeeL-A (SEQ ID NO:57) and downstream homology arm primers DN-yeeL-S(SEQ ID NO:58) and DN-yeeL-A(SEQ ID NO:59) were designed according to upstream and downstream sequences of its yeeL gene. The upstream and downstream homology arms of the yeeL gene were amplified. Primers ppc-S(SEQ ID NO: 60) and ppc-A (SEQ ID NO: 61) were designed according to the ppc gene, and the ppc gene fragment (SEQ ID NO: 5) was amplified. Promoter $P_{trc}$ was designed in the downstream primer of the yeeL gene upstream homology arm and the ppc gene upstream primer. The integrated fragment (yeeL gene upstream homology arm-$P_{trc}$-ppc-yeeL gene downstream homology arm) of the ppc gene was obtained by overlapping PCR of the above fragments. A DNA fragment which was used for constructing pGRB-yeeL and contained a target sequence was obtained by annealing primers gRNA-yeeL-S(SEQ ID NO:62) and gRNA-yeeL-A (SEQ ID NO:63). The DNA fragment was recombined with a linearized pGRB vector to obtain recombinant pGRB-yghE. The integrated fragment and pGRB-yeeL were electrotransformed into E. coli SAR7 competent cells containing a pREDCas9 vector. The resuscitated strains after electrotransformation were coated on an LB plate containing ampicillin and spectinomycin and cultured overnight at 32° C., and the positive recons were verified via PCR. Subsequently pGRB-yeeL and pREDCas9 used for gene editing were eliminated, so as to finally obtain strain E. coli SAR8.

Figure 8:
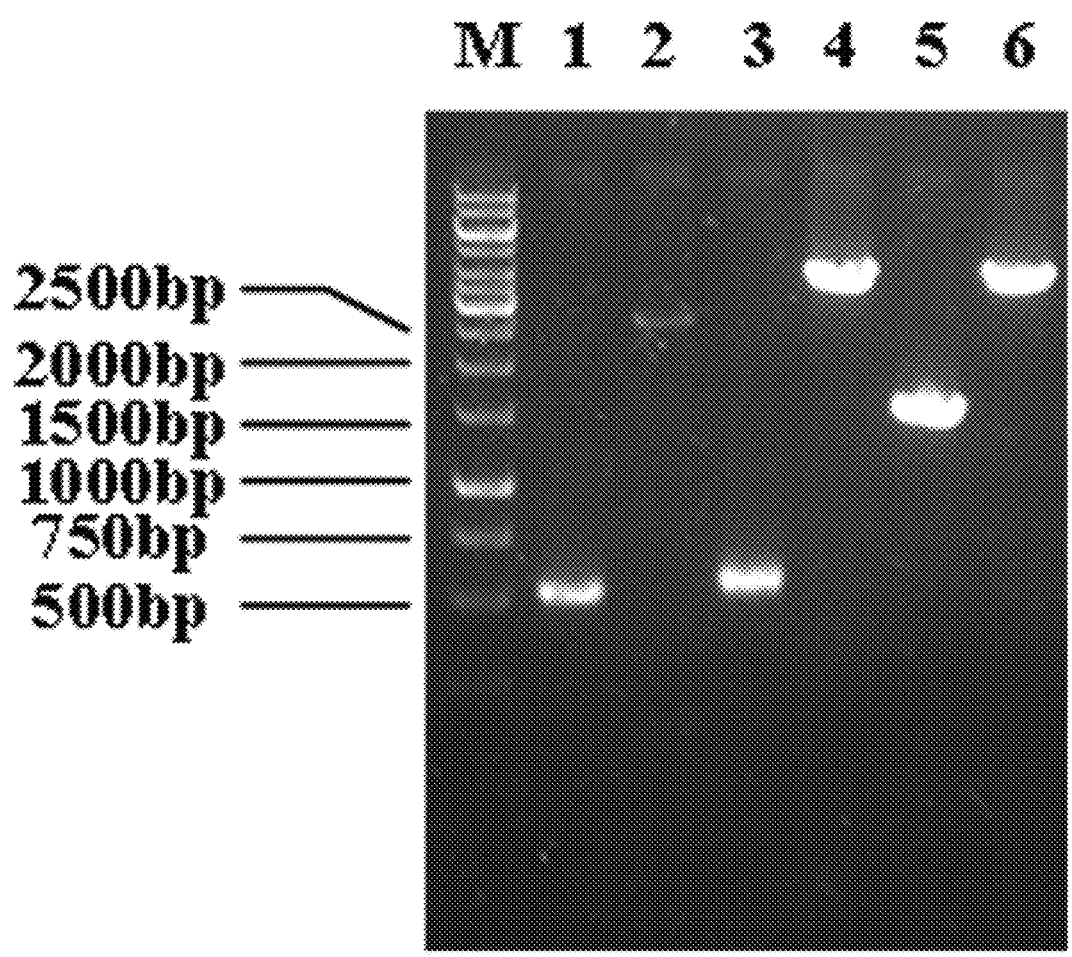
FIG. 8 is a yeeL::P$_{trc}$-ppc integration electrophortogram in the disclosure; in which, M-1 kb Maker; 1-upstream homology arm; 2-target gene; 3-downstream homology arm; 4-overlapped fragment; 5-protobacterium PCR fragment; 6-PCR fragment of target strain.

The electrophortogram of the construction of the $P_{trc}$-ppc integrated fragment and the PCR verification of the positive strains was as shown in FIG. 8. Wherein, the length of the upstream homology arm is 533 bp, the length of the ppc gene fragment is 2770 bp, the length of the downstream homology arm is 581 bp, and the total length of the integrated fragment is 381 bp. When in PCR verification, the length of the fragment subjected to PCR amplification by positive bacteria is 3813 bp, and the length of the fragment subjected to PCR amplification by protobacteria is 1613 bp.

2.9 Knockout of pykF Gene

An E. coli ATCC27325 genome was used as a template. Upstream homology arm primers UP-pykF-S(SEQ ID NO: 64) and UP-pykF-A (SEQ ID NO: 65) and downstream homology arm primers DN-pykF-S(SEQ ID NO: 66) and DN-pykF-A (SEQ ID NO: 67) were designed according to upstream and downstream sequences of its pykF gene, and the upstream and downstream homology arms of the pykF gene were amplified. The pykF gene knockout fragment (pykF gene upstream homology arm-pykF gene downstream homology arm) was obtained by overlapping PCR. A DNA fragment which was used for constructing pGRB-pykF and contained a target sequence was obtained by annealing primers gRNA-pykF-S(SEQ ID NO:68) and gRNA-pykF-A (SEQ ID NO:69). The DNA fragment was recombined with a linearized pGRB vector to obtain recombinant pGRB-pykF. The integrated fragment and pGRB-pykF were electrotransformed into E. coli SAR8 competent cells containing a pREDCas9 vector. The resuscitated strains after electrotransformation were coated on an LB plate containing ampicillin and spectinomycin and cultured overnight at 32° C., and the positive recons were verified via PCR. Subsequently pGRB-pykF and pREDCas9 used for gene editing were eliminated, so as to finally obtain strain E. coli SAR9.

Figure 9:
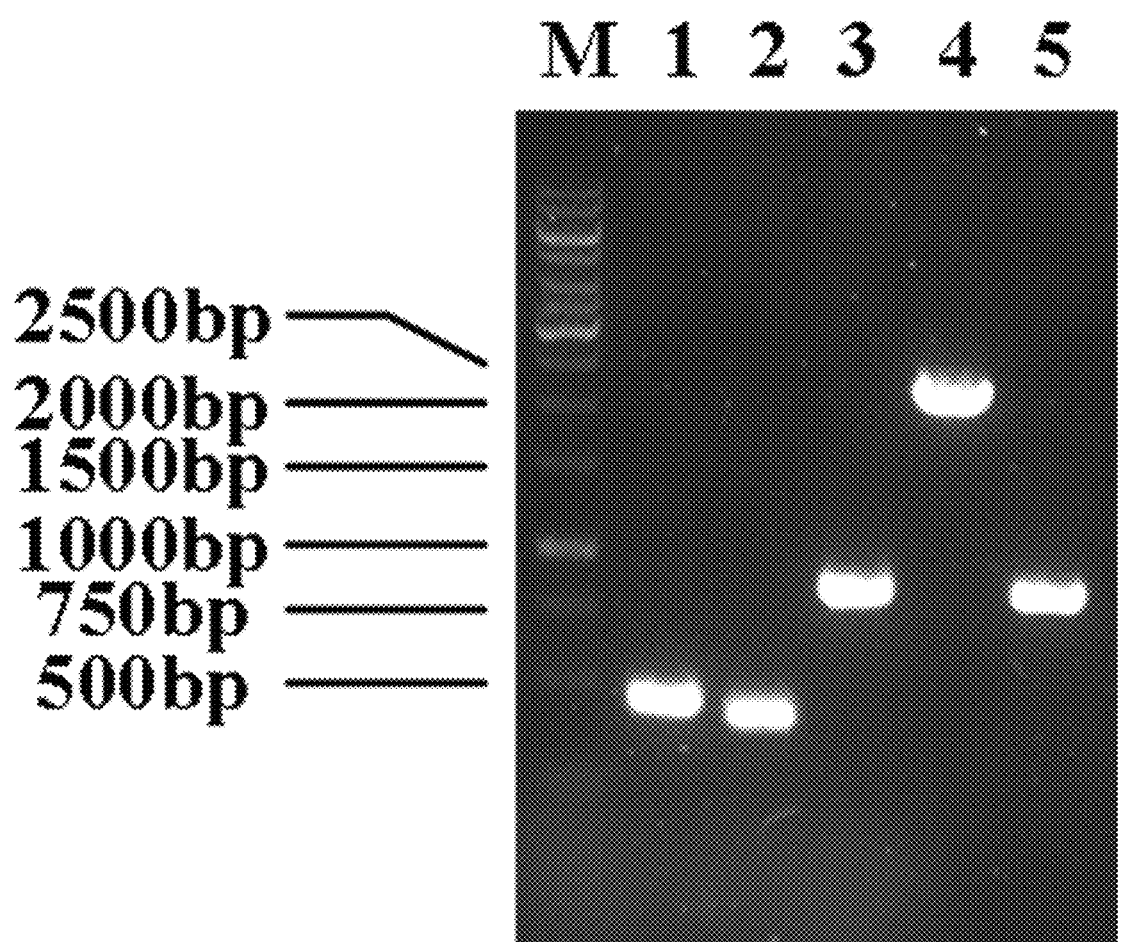
FIG. 9 is a pykF knockout electrophortogram of the disclosure; in which, M-1 kb Maker; 1-upstream homology arm; 2-downstream homology arm; 3-overlapped fragment; 4-protobacterium PCR fragment; 5-PCR fragment of target strain.

The electrophortogram of the construction of the pykF gene knockout fragment and the PCR verification of the positive strains was as shown in FIG. 9. Wherein, the length of the upstream homology arm is 471 bp, the length of the downstream homology arm is 429 bp, and the total length of the gene knockout fragment is 856 bp. When in PCR verification, the length of the fragment subjected to PCR amplification by positive bacteria is 856 bp, and the length of the fragment subjected to PCR amplification by protobacteria is 2180 bp.

3. Primers Used in the Construction Process of Strains

All primers involved in the construction process of strains are shown in Table as follows:

| SEQ ID NO: | Primers | Sequence (5'-3') |
|---|---|---|
| 6 | UP-mbhA-S | GCCAGCACGAACATAATCCC |
| 7 | UP-mbhA-A | TAAAGTTAAACAAAATTATTT CTAGACCCTATAGTGAGTCGT ATTACACGGTGGCAGGTTTT GG |
| 8 | DN-mbhA-S | TGGGGCCTCTAAACGGGTCT TGAGGGGTTTTTTGGACCAA AAGTGCGTCCGATAC |
| 9 | DN-mbhA-A | CGGCGTAATCACAAACTGGC |
| 10 | dpkA-S | TAGGGTCTAGAAATAATTTTG TTTAACTTTAAGAAGGAGATA TACCATGACGAACGAACCGG ACC |
| 11 | dpkA-A | AGACCCGTTTAGAGGCCCCA AGGGGTTATGCTAGTTATTCG AACAGACTGCGGATG |
| 12 | gRNA-mbhA-S | AGTCCTAGGTATAATACTAGT TACCGGGCATACCGATGCGA GTTTTAGAGCTAGAA |

| SEQ ID NO: | Primers | Sequence (5'-3') |
|---|---|---|
| 13 | gRNA-mbhA-A | TTCTAGCTCTAAAACTCGCATCGGTATGCCCGGTAACTAGTATTATACCTAGGACT |
| 14 | UP-ylbE-S | ACCCAACCTTACGCAACCAG |
| 15 | UP-ylbE-A | AATTGTTATCCGCTCACAATTCCACACATTATACGAGCCGGATGATTAATTGTCAATTGTTCGATAACCGCAGCAT |
| 16 | DN-ylbE-S | AAAGACTGGGCCTTTCGTTTTATCTGTTGTTTGTCGGTGAACGCTCTCCTGAGTAGGACAAATCGCTGGCGTGCTTTGAA |
| 17 | DN-ylbE-A | GGCGTAACTCAGCAGGCAG |
| 18 | gltA-S | TCCGGCTCGTATAATGTGTGGAATTGTGAGCGGATAACAATTTCACACAGGAAACAGACCATGGCTGATACAAAAGCAAAACTC |
| 19 | gltA-A | CACCGACAAACAACAGATAAAACGAAAGGCCCAGTCTTTCGACTGAGCCTTTCGTTTTATTTGTTAACGCTTGATATCGCTTTTAAAG |
| 20 | gRNA-ylbE-S | AGTCCTAGGTATAATACTAGTACACTGGCTGGATGTGCAACGTTTTAGAGCTAGAA |
| 21 | gRNA-ylbE-A | TTCTAGCTCTAAAACGTTGCACATCCAGCCAGTGTACTAGTATTATACCTAGGACT |
| 22 | UP-iclR-S | CGTGGAGTTGAAGGTGTTGGT |
| 23 | UP-iclR-A | TCCTTCGCCGCTTTAATCACCGGCAATCCACTCCAGTAATT |
| 24 | DN-iclR-S | AATTACTGGAGTGGATTGCCGGTGATTAAAGCGGCGAAGGA |
| 25 | DN-iclR-A | TAATAGAGGCGTCGCCAGCT |
| 26 | gRNA-iclR-S | AGTCCTAGGTATAATACTAGTACGGAACTGGCGCAACAAGCGTTTTAGAGCTAGAA |
| 27 | gRNA-iclR-A | TTCTAGCTCTAAAACGCTTGTTGCGCCAGTTCCGTACTAGTATTATACCTAGGACT |
| 28 | UP-aceB-S | GAGCTGGCGTAGTCACGGTAA |
| 29 | UP-aceB-A | TTCGCTGGCAATGACTTTCACAGAAGTTTATTGCGTTGTGGC |
| 30 | DN-aceB-S | GCCACAACGCAATAAACTTCTGTGAAAGTCATTGCCAGCGAA |
| 31 | DN-aceB-A | GCACGACGGAAGGTGTTGTT |
| 32 | gRNA-aceB-S | AGTCCTAGGTATAATACTAGTCCAGCTCAAGCCCAATCCAGGTTTTAGAGCTAGAA |
| 33 | gRNA-aceB-A | TTCTAGCTCTAAAACCTCGCGGCCAGATACGCATGACTAGTATTATACCTAGGACT |
| 34 | UP-yeeP-S | GGTCAGGAGGTAACTTATCAGCG |
| 35 | UP-yeeP-A | AATTGTTATCCGCTCACAATTCCACACATTATACGAGCCGGATGATTAATTGTCAAATGGCAGGGCTCCGTTTT |
| 36 | DN-yeeP-S | AAAGACTGGGCCTTTCGTTTTATCTGTTGTTTGTCGGTGAACGCTCTCCTGAGTAGGACAAATGAACTGGATTTTCTTCTGAACCTGT |
| 37 | DN-yeeP-A | ACGATGTCAGCAGCCAGCA |
| 38 | aceA-S | TCCGGCTCGTATAATGTGTGGAATTGTGAGCGGATAACAATTTCACACAGGAAACAGACCATGAAAACCCGTACACAACAAATT |
| 39 | aceA-A | CACCGACAAACAACAGATAAAACGAAAGGCCCAGTCTTTCGACTGAGCCTTTCGTTTTATTTGTTAGAACTGCGATTCTTCAGTGG |
| 40 | gRNA-yeeP-S | AGTCCTAGGTATAATACTAGTACAGAATATTCGCGAAAAAAGTTTTAGAGCTAGAA |
| 41 | gRNA-yeeP-A | TTCTAGCTCTAAAACTTTTTTCGCGAATATTCTGTACTAGTATTATACCTAGGACT |
| 42 | UP-yghE-S | GTCAGGCACTGGCGAAAGAT |
| 43 | UP-yghE-A | AATTGTTATCCGCTCACAATTCCACACATTATACGAGCCGGATGATTAATTGTCAACGCAAGCCATAAACCCACA |
| 44 | DN-yghE-S | CTGGGCCTTTCGTTTTATCTGTTGTTTGTCGGTGAACGCTCTCCTGAGTAGGACAAATTTCCGACATCGAAATGCGT |
| 45 | DN-yghE-A | AGGCGTTGTTGTGGCAGATT |
| 46 | pntAB-S | TCCGGCTCGTATAATGTGTGGAATTGTGAGCGGATAACAATTTCACACAGGAAACAGACCATGCGAATTGGCATACCAAGA |
| 47 | pntAB-A | ACAAACAACAGATAAAACGAAAGGCCCAGTCTTTCGACTGAGCCTTTCGTTTTATTTGTTACAGAGCTTTCAGGATTGCATC |
| 48 | gRNA-yghE-S | AGTCCTAGGTATAATACTAGTGCTGAAAAAATATCGCCCACGTTTTAGAGCTAGAA |
| 49 | gRNA-yghE-A | TTCTAGCTCTAAAACGTGGGCGATATTTTTTCAGCACTAGTATTATACCTAGGACT |
| 50 | UP-ycdW-S | TCCTTCAGCCACTCGGACAC |
| 51 | UP-ycdW-A | GATAGCAGGAATCCTGATGCTTTATGGATGCGATAATCGTCAAAAC |

| SEQ ID NO: | Primers | Sequence (5'-3') |
|---|---|---|
| 52 | DN-ycdW-S | GTTTTGACGATTATCGCATCCATAAAGCATCAGGATTCCTGCTATC |
| 53 | DN-ycdW-A | ATTATCCGTTGCAGTTATGAGTGA |
| 54 | gRNA-ycdW-S | AGTCCTAGGTATAATACTAGTTTGCTCAGAGTCTGCAAACCGTTTTAGAGCTAGAA |
| 55 | gRNA-ycdW-A | TTCTAGCTCTAAAACGGTTTGCAGACTCTGAGCAAACTAGTATTATACCTAGGACT |
| 56 | UP-yeeL-S | TTCATCGGGACGAGTGGAGA |
| 57 | UP-yeeL-A | AATTGTTATCCGCTCACAATTCCACACATTATACGAGCCGGATGATTAATTGTCAACCATAGCATCGCCAATCTGA |
| 58 | DN-yeeL-S | CTGGGCCTTTCGTTTTATCTGTTGTTTGTCGGTGAACGCTCTCCTGAGTAGGACAAATACCCAAAGGTGAAGATAAAGCC |
| 59 | DN-yeeL-A | CATTCCCTCTACAGAACTAGCCCT |
| 60 | ppc-S | TCCGGCTCGTATAATGTGTGGAATTGTGAGCGGATAACAATTTCACACAGGAAACAGACCATGAACGAACAATATTCCGCAT |
| 61 | ppc-A | ACAAACAACAGATAAAACGAAAGGCCCAGTCTTTCGACTGAGCCTTTCGTTTTATTTGTTAGCCGGTATTACGCATACCT |
| 62 | gRNA-yeeL-S | AGTCCTAGGTATAATACTAGTAACACAGCAATACGGTACGCGTTTTAGAGCTAGAA |
| 63 | gRNA-yeeL-A | TTCTAGCTCTAAAACGCGTACCGTATTGCTGTGTTACTAGTATTATACCTAGGACT |
| 64 | UP-pykF-S | ACTGACAACTTCGGCACCAGA |
| 65 | UP-pykF-A | CAGATGCGGTGTTAGTAGTGCCTCTTCAGATTCGGTTTTCGGTC |
| 66 | DN-pykF-S | GACCGAAAACCGAATCTGAAGAGGCACTACTAACACCGCATCTG |
| 67 | DN-pykF-A | AACCTGCCAGCAGAGTAGAACC |
| 68 | gRNA-pykF-S | AGTCCTAGGTATAATACTAGTCGCAACGTGATGAGCAAAACGTTTTAGAGCTAGAA |
| 69 | gRNA-pykF-A | TTCTAGCTCTAAAACGTTTTGCTCATCACGTTGCGACTAGTATTATACCTAGGACT |

Example 2: Production of Sarcosine by Flask Fermentation Using Strain E. coli SAR Fermentation Experiment of Strain E. coli SAR in a 5 L Fermentor:

Slope activation culture: a ring of bacteria were scrapped off from a preserving tube in a −80° C. refrigerator, evenly coated on an activated slope, cultured for 12 h at 37° C., and then transferred to an eggplant-shaped bottle to conduct further culture for 12 h;

Seed culture: a proper amount of sterile water was placed in the eggplant-shaped bottle, and the bacterial suspension was inoculated into a seed culture medium to culture for 6 h, wherein the pH is stabilized at about 7.0, the temperature is constant at 37° C., and the dissolved oxygen is between 25% and 35%;

Fermentation culture: a fresh fermentation culture medium was inoculated with an inoculation amount of 15%. The loading amount was 60% (v culture medium/v fermentor). During the fermentation, the pH was stably controlled at about 7.0, and the temperature was maintained at 36.5-37.5° C. The dissolved oxygen is between 25% and 35%. When the glucose in the culture medium was completely consumed, 800 g/L glucose solution was fed for further culture, and the glucose concentration in the fermentation medium was maintained to be less than 3 g/L. When $OD_{600}$ is 40, 1.6 mol/L methylamine hydrochloride solution was fed at a flow rate of 25 mL/h with a feeding amount of 75 mL/L of culture medium. The fermentation period is 30 h;

The compositions of the slope culture medium: 1 g/L of glucose, 10 g/L of peptone, 10 g/L of beef extract, 5 g/L of yeast powder, 2.5 g/L of NaCl, 25 g/L of agar and the balance of water, and pH 7.0;

The compositions of the seed culture medium: 25/L of glucose, 5 g/L of yeast extract, 5 g/L of tryptone, 5 g/L of $KH_2PO_4$ 5 g/L, 2 g/L of $MgSO_4.7H_2O$ and the balance of water, and pH 7.0.

The compositions of the fermentation culture medium: 20 g/L of glucose, 4 g/L of yeast extract, 5 g/L of tryptone, 5 g/L of sodium citrate, 2 g/L of $KH_2PO_4$, 1 g/L of $MgSO_4.7H_2O$ and the balance of water, and pH 7.0.

Figure 10:
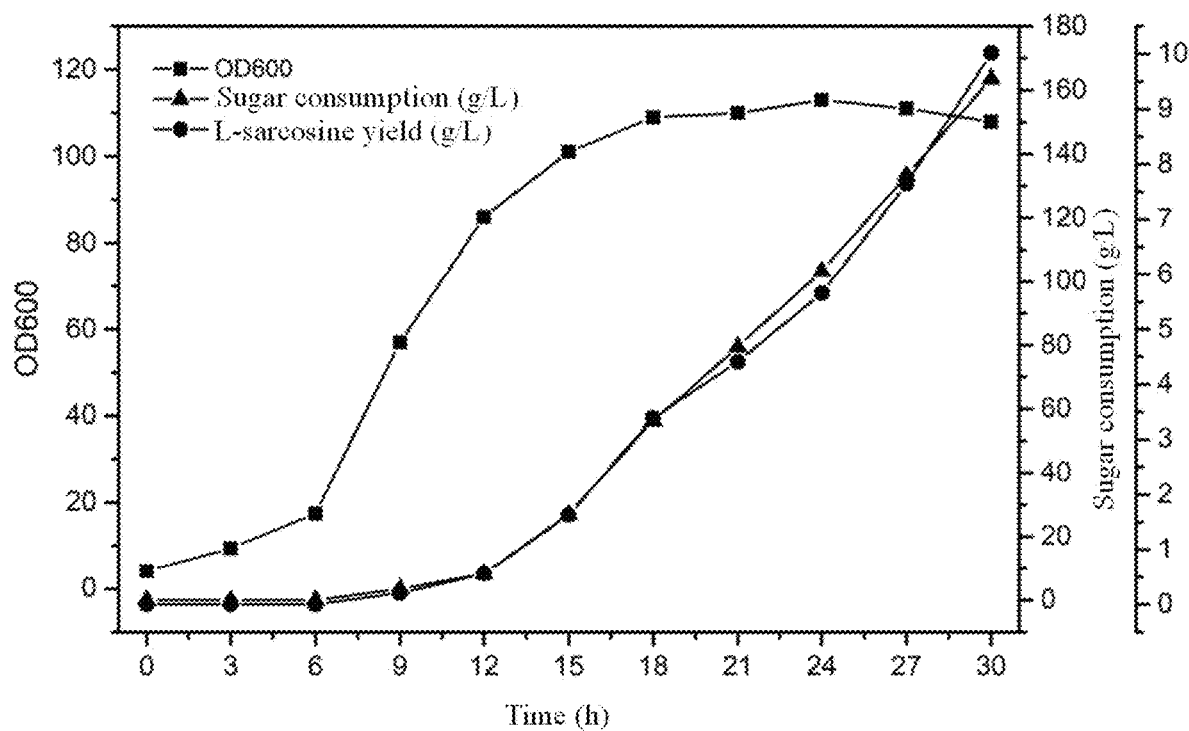
FIG. 10 is a fermentation process diagram of Example 2 in the disclosure.

After fermentation for 30 h in the 5 L fermentor, the sarcosine titer can reach 10 g/L. The fermentation process curve is shown in FIG. 10.

Although the embodiments of the disclosure are disclosed for illustrating the purposes, those skilled in the art should understand that various substitutions, changes and modifications are possible without departing from the spirit and scope of the disclosure and appended claims, therefore the scope of the disclosure is not limited to the contents disclosed in embodiments.

We claim:

1. A genetically engineered bacterium for synthesizing Sarcosine, wherein the genetically engineered bacterium is *Escherichia coli* SAR which is obtained by using *Escherichia coli* ATCC27325 as a host and through the following transformations: integrating singly copied imine reductase gene dpkA, which is controlled by T7 promoter, at the mbhA site on its genome; singly copying citrate synthase gene gltA, which is controlled by trc promoter, at the ylbE site; knocking out glyoxylate cycle inhibitor gene iclR; knocking out malate synthase gene aceB; singly copying isocitrate lyase gene aceA, which is controlled by trc promoter, at the yeeP site; singly copying membrane-bound transhydrogenase gene pntAB, which is controlled by trc promoter, at the yghE site; knocking out 2-ketate reductase gene ycdW; singly copying phosphoenolpyruvate carboxylase gene ppc, which is controlled by controlled by trc promoter, at the yeeL site; and knocking out pyruvate kinase gene pykF;

the imine reductase gene dpkA has a nucleotide sequence of SEQ ID NO: 1;

the citrate synthase gene gltA has a nucleotide sequence of SEQ ID NO: 2;

the isocitrate lyase gene aceA has a nucleotide sequence of SEQ ID NO: 3;

the membrane-bound transhydrogenase gene pntAB has a nucleotide sequence of SEQ ID NO:4;

the phosphoenolpyruvate carboxylase gene ppc has a nucleotide sequence of SEQ ID NO:5.

2. A method for constructing a genetically engineered bacterium for synthesizing Sarcosine according to claim 1, wherein the method uses a CRISPR/Cas9-mediated gene editing technology to perform targeted transformation on *Escherichia coli*, comprising the following steps:

(1) introducing a single copy of a imine reductase gene dpkA derived from *Brevibacterium* linens ATCC 9172 at the mbhA site on *Escherichia coli* ATCC27325 genome, wherein the dpkA has the sequence of SEQ ID NO:1, and is controlled by T7 promoter;

(2) introducing a single copy of the endogenous citrate synthase gene gltA at the ylbE site on *Escherichia coli*

ATCC27325 genome, wherein the qltA has the sequence of SEQ ID NO:2, and is controlled by trc promoter;

(3) performing gene knockout at the iclR site on *Escherichia coli* ATCC27325 genome;

(4) performing gene knockout at the aceB site on *Escherichia coli* ATCC27325 genome;

(5) introducing a single copy of the endogenous isocitrate lyase gene aceA at the yeeP site on *Escherichia coli* ATCC27325 genome, wherein the aceA has the sequence of SEQ ID NO:3 and is controlled by trc promoter;

(6) introducing a single copy of the endogenous membrane-bound transhydrogenase gene pntAB at the yghE site on *Escherichia coli* ATCC27325 genome, wherein the pntAB has the sequence of SEQ ID NO:4 and is controlled by trc promoter;

(7) performing gene knockout at the ycdW site on *Escherichia coli* ATCC27325 genome;

(8) introducing a single copy of endogenous phosphoenolpyruvate carboxylase gene ppc at the yeeL site on *Escherichia coli* ATCC27325 genome, wherein the ppc has the sequence of SEQ ID NO:5, and is controlled by trc promoter; and (9) performing gene knockout at the pykF site on *Escherichia coli* ATCC27325 genome.

3. A method for producing Sarcosine by fermenting the genetically engineered bacterium according to claim 1, comprising the following steps:

Inoculating the fermentation culture, wherein a starter culture of the genetically engineered bacteria of claim 1 is inoculated into a fresh fermentation culture medium in an inoculation amount of 15-20%;

performing the fermentation under the following conditions to obtain sarcosine:

controlling the pH at 6.8-7.2;

maintaining the temperature is maintained at 36.5-37.5° C., and the dissolved oxygen between 25% and 35%;

when the glucose in the culture medium is completely consumed, adding glucose via a solution of 700-800 g/L glucose, wherein the concentration of glucose in the fermentation culture medium is maintained to be <3 g/L;

when the culture reaches an $OD_{600}=40$, feeding a solution of 1.5-1.6 mol/L methylaminehydrochloride at a flow rate of 20-25 mL/h with a feeding amount of 75 mL/L culture medium; and, wherein the fermentation period is 28-32 h;

wherein the composition of the fermentation culture medium is: 15-25 g/L of glucose, 1-5 g/L of tryptone, 3-5 g/L of sodium citrate, 1-5 g/L of KH2POs, 0.1-1 g/L of MgSO4*7H2O and the balance of water, and pH 7.0-7.2.

* * * * *

SEQUENCE LISTING

<160> NUMBER OF SEQ ID NOS: 69

<210> SEQ ID NO 1
<211> LENGTH: 1005
<212> TYPE: DNA

<213> ORGANISM: Artificial sequence
<220> FEATURE:
<223> OTHER INFORMATION: synthesized

<400> SEQUENCE: 1

```
atgacgaacg aaccggaccg catcagcttc gacgatctgg ttagcgccat tcaagccaaa      60
ctggtggccg cgggtgccag tccaagtgtt gccgaagttc tggcgacgaa ttgcgccacg     120
tgcgaacgcg atggcacgct gagccacggt gtgttccgtg ttgccggcta tctggatagt     180
ctgacccgtg gttgggccga tggtgccgcc gaaccgaata tcgatgttgt gggcccgagc     240
tacatccgta tcgatggccg caatggtttc gcgcaaccag cgctggccga agcccgtcca     300
accattgatg aggccctcgc ggaaagtggt gttgccgtta tcgcgctgcg cagcacgcat     360
cactttagcg cgctgtggcc agatctggag agcttcgccc gcgaaggccg cgttgccatg     420
ggtatgattg cgagcggcaa actggccgtt gttccggaag gtgccacccg cccagttttc     480
agcaccaacc cgtttggctt tgccaccca gttgcgggtg ccgacccaat tgtgttcgac     540
ttcagtacca gcagcatgag ccacggcgat ctgcaactgc tgcgtgccga aggtcgcgat     600
gttccggttg gcaccggcgt tgatagcacg ggtgccgatg ccaccgaccc aaatgccatt     660
ctggatggtg gcggcattcg tccaattggc ggccataaag gcgcgctgct cagcttcatg     720
attgaaaccc tcgccgccgg tctgacgggt ggtgcgttca cctacgaaat tgatgccgaa     780
gcgccggaag gtgcgcacac ctttcgcacc ggccagctgt ttatcgtgat cgacccagaa     840
cgtggcggta tgatgcgta tctgggtcgt gttcgcgaat tcgtggaaat gctgcgcgat     900
gccggtatgg atcgtcaacc gggcgatcgc cgttacgcca atcgtgcgga agcggccgtt     960
cgcggtatcc cagtgacgga taccatccgc agtctgttcg aataa                   1005
```

<210> SEQ ID NO 2
<211> LENGTH: 1284
<212> TYPE: DNA
<213> ORGANISM: Artificial sequence
<220> FEATURE:
<223> OTHER INFORMATION: synthesized

<400> SEQUENCE: 2

```
atggctgata caaaagcaaa actcaccctc aacggggata cagctgttga actggatgtg      60
ctgaaaggca cgctgggtca agatgttatt gatatccgta ctctcggttc aaaaggtgtg     120
ttcacctttg acccaggctt cacttcaacc gcatcctgcg aatctaaaat tacttttatt     180
gatggtgatg aaggtatttt gctgcaccgc ggtttcccga tcgatcagct ggcgaccgat     240
tctaactacc tggaagtttg ttacatcctg ctgaatggtg aaaaaccgac tcaggaacag     300
tatgacgaat ttaaaactac ggtgacccgt cataccatga tccacgagca gattacccgt     360
ctgttccatg ctttccgtcg cgactcgcat ccaatggcag tcatgtgtgg tattaccggc     420
gcgctggcgg cgttctatca cgactcgctg atgttaaca atcctcgtca ccgtgaaatt     480
gccgcgttcc gcctgctgtc gaaaatgccg accatggccg cgatgtgtta caagtattcc     540
attggtcagc catttgttta cccgcgcaac gatctctcct acgccggtaa cttcctgaat     600
atgatgttct ccacgccgtg cgaaccgtat gaagttaatc cgattctgga cgtgctatg     660
gaccgtattc tgatcctgca cgctgaccat gaacagaacg cctctacctc caccgtgcgt     720
accgctggct cttcgggtgc gaacccgttt gcctgtatcg cagcaggtat tgcttcactg     780
tggggacctg cgcacggcgg tgctaacgaa gcggcgctga aatgctggga gaaatcagc     840
tccgttaaac acattccgga atttgttcgt cgtgcgaaag acaaaatga ttcttttccgc     900
```

```
ctgatgggct tcggtcaccg cgtgtacaaa aattacgacc cgcgcgccac cgtaatgcgt    960
gaaacctgcc atgaagtgct gaaagagctg ggcacgaagg atgacctgct ggaagtggct   1020
atggagctgg aaaacatcgc gctgaacgac ccgtacttta tcgagaagaa actgtacccg   1080
aacgtcgatt tctactctgg tatcatcctg aaagcgatgg gtattccgtc ttccatgttc   1140
accgtcattt tcgcaatggc acgtaccgtt ggctggatcg cccactggag cgaaatgcac   1200
agtgacggta tgaagattgc ccgtccgcgt cagctgtata caggatatga aaacgcgac    1260 tttaaaagcg atatcaagcg ttaa                                         1284
```

<210> SEQ ID NO 3
<211> LENGTH: 1305
<212> TYPE: DNA
<213> ORGANISM: Artificial sequence
<220> FEATURE:
<223> OTHER INFORMATION: synthesized

<400> SEQUENCE: 3

```
atgaaaaccc gtacacaaca aattgaagaa ttacagaaag agtggactca accgcgttgg     60
gaaggcatta ctcgcccata cagtgcggaa gatgtggtga aattacgcgg ttcagtcaat    120
cctgaatgca cgctggcgca actgggcgca gcgaaaatgt ggcgtctgct gcacggtgag    180
tcgaaaaaag gctacatcaa cagcctcggc gcactgactg cggtcaggc gctgcaacag    240 gcgaaagcgg gtattgaagc agtctatctg tcgggatggc aggtagcggc ggacgctaac    300
ctggcggcca gcatgtatcc ggatcagtcg ctctatccgg caaactcggt gccagctgtg    360
gtggagcgga tcaacaacac cttccgtcgt gccgatcaga tccaatggtc cgcgggcatt    420
gagccgggcg atccgcgcta tgtcgattac ttcctgccga tcgttgccga tgcggaagcc    480
ggttttggcg gtgtcctgaa tgcctttgaa ctgatgaaag cgatgattga agccggtgca    540
gcggcagttc acttcgaaga tcagctggcg tcagtgaaga atgcggtca catgggcggc    600 aaagttttag tgccaactca ggaagctatt cagaaactgg tcgcggcgcg tctggcagct    660
gacgtgacgg gcgttccaac cctgctggtt gcccgtaccg atgctgatgc ggcggatctg    720
atcacctccg attgcgaccc gtatgacagc gaatttatta ccggcgagcg taccagtgaa    780
ggcttcttcc gtactcatgc gggcattgag caagcgatca gccgtggcct ggcgtatgcg    840
ccatatgctg acctggtctg tgtgtgaaacc tccacgccgg atctggaact ggcgcgtcgc    900
tttgcacaag ctatccacgc gaaatatccg ggcaaactgc tggcttataa ctgctcgccg    960
tcgttcaact ggcagaaaaa cctcgacgac aaaactattg ccagcttcca gcagcagctg   1020
tcggatatgg gctacaagtt ccagttcatc accctggcag gtatccacag catgtggttc   1080
aacatgtttg acctggcaaa cgcctatgcc cagggcgagg gtatgaagca ctacgttgag   1140
aaagtgcagc agccggaatt tgccgccgcg aaagatggct ataccttcgt atctcaccag   1200
caggaagtgg gtacaggtta cttcgataaa gtgacgacta ttattcaggg cggcacgtct   1260
tcagtcaccg cgctgaccgg ctccactgaa gaatcgcagt tctaa                 1305
```

<210> SEQ ID NO 4
<211> LENGTH: 2932
<212> TYPE: DNA
<213> ORGANISM: Artificial sequence
<220> FEATURE:
<223> OTHER INFORMATION: synthesized

<400> SEQUENCE: 4

-continued

```
atgcgaattg gcataccaag agaacggtta accaatgaaa cccgtgttgc agcaacgcca    60
aaaacagtgg aacagctgct gaaactgggt tttaccgtcg cggtagagag cggcgcgggt   120
caactggcaa gttttgacga taaagcgttt gtgcaagcgg gcgctgaaat tgtagaaggg   180
aatagcgtct ggcagtcaga gatcattctg aaggtcaatg cgccgttaga tgatgaaatt   240
gcgttactga atcctgggac aacgctggtg agttttatct ggcctgcgca gaatccggaa   300
ttaatgcaaa aacttgcgga acgtaacgtg accgtgatgg cgatggactc tgtgccgcgt   360
atctcacgcg cacaatcgct ggacgcacta agctcgatgg cgaacatcgc cggttatcgc   420
gccattgttg aagcggcaca tgaatttggg cgcttcttta ccgggcaaat tactgcggcc   480
gggaaagtgc caccggcaaa agtgatgtg attggtgcgg gtgttgcagg tctggccgcc    540
attggcgcag caacagtct cggcgcgatt gtgcgtgcat tcgacacccg cccggaagtg   600
aaagaacaag ttcaaagtat gggcgcggaa ttcctcgagc tggattttaa agaggaagct   660
ggcagcggcg atggctatgc caaagtgatg tcggacgcgt tcatcaaagc ggaaatggaa   720
ctctttgccg cccaggcaaa agaggtcgat atcattgtca ccaccgcgct tattccaggc   780
aaaccagcgc cgaagctaat tacccgtgaa atggttgact ccatgaaggc gggcagtgtg   840
attgtcgacc tggcagccca aaacggcggc aactgtgaat acaccgtgcc gggtgaaatc   900
ttcactacgg aaaatggtgt caaagtgatt ggttataccg atcttccggg ccgtctgccg   960
acgcaatcct cacagcttta cggcacaaac ctcgttaatc tgctgaaact gttgtgcaaa  1020
gagaaagacg gcaatatcac tgttgatttt gatgatgtgg tgattcgcgg cgtgaccgtg  1080
atccgtgcgg gcgaaattac ctggccggca ccgccgattc aggtatcagc tcagccgcag  1140
gcggcacaaa aagcggcacc ggaagtgaaa actgaggaaa aatgtacctg ctcaccgtgg  1200
cgtaaatacg cgttgatggc gctggcaatc attcttttg gctggatggc aagcgttgcg  1260
ccgaaagaat tccttgggca cttcaccgtt ttcgcgctgg cctgcgttgt cggttattac  1320
gtggtgtgga atgtatcgca cgcgctgcat acaccgttga tgtcggtcac caacgcgatt  1380
tcagggatta ttgttgtcgg agcactgttg cagattggcc agggcggctg ggttagcttc  1440
cttagtttta tcgcggtgct tatagccagc attaatattt tcggtggctt caccgtgact  1500
cagcgcatgc tgaaaatgtt ccgcaaaaat taagggtaa catatgtctg gaggattagt  1560
tacagctgca tacattgttg ccgcgatcct gtttatcttc agtctggccg gtctttcgaa  1620
acatgaaacg tctcgccagg gtaacaactt cggtatcgcc gggatggcga ttgcgttaat  1680
cgcaaccatt tttggaccgg atacgggtaa tgttggctgg atcttgctgg cgatggtcat  1740
tggtggggca attggtatcc gtctggcgaa gaaagttgaa atgaccgaaa tgccagaact  1800
ggtggcgatc ctgcatagct tcgtgggtct ggcggcagtg ctggttggct ttaacagcta  1860
tctgcatcat gacgcgggaa tggcaccgat tctggtcaat attcacctga cggaagtgtt  1920
cctcggtatc ttcatcgggg cggtaacgtt cacgggttcg gtggtggcgt tcggcaaact  1980
gtgtggcaag atttcgtcta aaccattgat gctgccaaac cgtcacaaaa tgaacctggc  2040
ggctctggtc gtttccttcc tgctgctgat tgtatttgtt cgcacggaca cgtcggcct   2100 gcaagtgctg gcattgctga taatgaccgc aattgcgctg gtattcggct ggcatttagt  2160
cgcctccatc ggtggtgcag atatgccagt ggtggtgtcg atgctgaact cgtactccgg  2220
ctgggcggct gcggctgcgg gctttatgct cagcaacgac ctgctgattg tgaccggtgc  2280
gctggtcggt tcttcggggg ctatccttc ttacattatg tgtaaggcga tgaaccgttc  2340
ctttatcagc gttattgcgg gtggtttcgg caccgacggc tcttctactg gcgatgatca  2400
```

```
ggaagtgggt gagcaccgcg aaatcaccgc agaagagaca gcggaactgc tgaaaaactc    2460
ccattcagtg atcattactc cggggtacgg catggcagtc gcgcaggcgc aatatcctgt    2520
cgctgaaatt actgagaaat tgcgcgctcg tggtattaat gtgcgtttcg gtatccaccc    2580
ggtcgcgggg cgtttgcctg acatatgaaa cgtattgctg gctgaagcaa aagtaccgta    2640
tgacatcgtg ctggaaatgg acgagatcaa tgatgacttt gctgataccg ataccgtact    2700
ggtgattggt gctaacgata cggttaaccc ggcggcgcag gatgatccga agagtccgat    2760
tgctggtatg cctgtgctgg aagtgtggaa agcgcagaac gtgattgtct ttaaacgttc    2820
gatgaacact ggctatgctg gtgtgcaaaa cccgctgttc ttcaaggaaa acacccacat    2880
gctgtttggt gacgccaaag ccagcgtgga tgcaatcctg aaagctctgt aa            2932
```

<210> SEQ ID NO 5
<211> LENGTH: 2652
<212> TYPE: DNA
<213> ORGANISM: Artificial sequence
<220> FEATURE:
<223> OTHER INFORMATION: synthesized

<400> SEQUENCE: 5

```
atgaacgaac aatattccgc attgcgtagt aatgtcagta tgctcggcaa agtgctggga     60
gaaaccatca aggatgcgtt gggagaacac attcttgaac gcgtagaaac tatccgtaag    120
ttgtcgaaat cttcacgcgc tggcaatgat gctaaccgcc aggagttgct caccaccttg    180
caaaatttgt cgaacgacga gctgctgccc gttgcgcgtg cgtttagtca gttcctgaac    240
ctggccaaca ccgccgagca ataccacagc atttcgccga aaggcgaagc tgccagcaac    300
ccggaagtga tcgcccgcac cctgcgtaaa ctgaaaaacc agccggaact gagcgaagac    360
accatcaaaa agcagtggga atcgctgtcg ctggaactgg tcctcacggc tcacccaacc    420
gaaattaccc gtcgtacact gatccacaaa atggtggaag tgaacgcctg tttaaaacag    480
ctcgataaca agatatcgc tgactacgaa cacaaccagc tgatgcgtcg cctgcgccag    540
ttgatcgccc agtcatggca taccgatgaa atccgtaagc tgcgtccaag cccggtagat    600
gaagccaaat ggggctttgc cgtagtggaa acagcctgtg gcaaggcgt accaaattac    660 ctgcgcgaac tgaacgaaca actggaagag aacctcggct acaaactgcc cgtcgaattt    720
gttccggtcc gttttacttc gtggatgggc ggcgaccgcg acggcaaccc gaacgtcact    780
gccgatatca cccgccacgt cctgctactc agccgctgga agccaccga tttgttcctg    840 aaagatattc aggtgctggt ttctgaactg tcgatggttg aagcgacccc tgaactgctg    900
gcgctggttg cgaagaagg tgccgcagaa ccgtatcgct atctgatgaa aaacctgcgt    960
tctcgcctga tggcgacaca ggcatggctg aagcgcgcc tgaaaggcga agaactgcca   1020
aaaccagaag gcctgctgac acaaaacgaa gaactgtggg aaccgctcta cgcttgctac   1080
cagtcacttc aggcgtgtgg catgggtatt atcgccaacg gcgatctgct cgacaccctg   1140
cgccgcgtga atgtttcgg cgtaccgctg gtccgtattg atatccgtca ggagagcacg   1200
cgtcataccg aagcgctggg cgagctgacc cgctacctcg gtatcggcga ctacgaaagc   1260
tggtcagagg ccgacaaaca ggcgttcctg atccgcgaac tgaactccaa acgtccgctt   1320
ctgccgcgca actggcaacc aagcgccgaa acgcgcgaag tgctcgatac ctgccaggtg   1380
attgccgaag caccgcaagg ctccattgcc gcctacgtga tctcgatggc gaaaacgccg   1440
tccgacgtac tggctgtcca cctgctgctg aaagaagcgg gtatcgggtt tgcgatgccg   1500
```

-continued

```
gttgctccgc tgtttgaaac cctcgatgat ctgaacaacg ccaacgatgt catgacccag    1560
ctgctcaata ttgactggta tcgtggcctg attcagggca acagatggt gatgattggc    1620 tattccgact cagcaaaaga tgcgggagtg atggcagctt cctgggcgca atatcaggca    1680
caggatgcat taatcaaaac ctgcgaaaaa gcgggtattg agctgacgtt gttccacggt    1740
cgcggcggtt ccattggtcg cggcggcgca cctgctcatg cggcgctgct gtcacaaccg    1800
ccaggaagcc tgaaaggcgg cctgcgcgta accgaacagg gcgagatgat ccgctttaaa    1860
tatggtctgc agaaatcac cgtcagcagc ctgtcgcttt ataccggggc gattctggaa     1920
gccaacctgc tgccaccgcc ggagccgaaa gagagctggc gtcgcattat ggatgaactg    1980
tcagtcatct cctgcgatgt ctaccgcggc tacgtacgtg aaaacaaaga ttttgtgcct    2040
tacttccgct ccgctacgcc ggaacaagaa ctgggcaaac tgccgttggg ttcacgtccg    2100
gcgaaacgtc gcccaaccgg cggcgtcgag tcactacgcg ccattccgtg gatcttcgcc    2160
tggacgcaaa accgtctgat gctccccgcc tggctgggtg caggtacggc gctgcaaaaa    2220
gtggtcgaag acgcaaaaca gagcgagctg gaggctatgt gccgcgattg gccattcttc    2280
tcgacgcgtc tcggcatgct ggagatggtc ttcgccaaag cagacctgtg gctggcggaa    2340
tactatgacc aacgcctggt agacaaagca ctgtggccgt taggtaaaga gttacgcaac    2400
ctgcaagaag aagacatcaa agtggtgctg gcgattgcca acgattccca tctgatggcc    2460
gatctgccgt ggattgcaga gtctattcag ctacggaata tttacaccga cccgctgaac    2520
gtattgcagg ccgagttgct gcaccgctcc cgccaggcag aaaagaagg ccaggaaccg     2580 gatcctcgcg tcgaacaagc gttaatggtc actattgccg ggattgcggc aggtatgcgt    2640
aataccggct aa                                                         2652
```

<210> SEQ ID NO 6
<211> LENGTH: 20
<212> TYPE: DNA
<213> ORGANISM: Artificial sequence
<220> FEATURE:
<223> OTHER INFORMATION: synthesized

<400> SEQUENCE: 6

```
gccagcacga acataatccc                                                   20
```

<210> SEQ ID NO 7
<211> LENGTH: 64
<212> TYPE: DNA
<213> ORGANISM: Artificial sequence
<220> FEATURE:
<223> OTHER INFORMATION: synthesized

<400> SEQUENCE: 7

```
taaagttaaa caaaattatt tctagaccct atagtgagtc gtattacacg gtggcaggtt      60
ttgg                                                                    64
```

<210> SEQ ID NO 8
<211> LENGTH: 55
<212> TYPE: DNA
<213> ORGANISM: Artificial sequence
<220> FEATURE:
<223> OTHER INFORMATION: synthesized

<400> SEQUENCE: 8

```
tggggcctct aaacgggtct tgaggggttt tttggaccaa aagtgcgtcc gatac           55
```

```
<210> SEQ ID NO 9
<211> LENGTH: 20
<212> TYPE: DNA
<213> ORGANISM: Artificial sequence
<220> FEATURE:
<223> OTHER INFORMATION: synthesized

<400> SEQUENCE: 9
cggcgtaatc acaaactggc                                              20

<210> SEQ ID NO 10
<211> LENGTH: 65
<212> TYPE: DNA
<213> ORGANISM: Artificial sequence
<220> FEATURE:
<223> OTHER INFORMATION: synthesized

<400> SEQUENCE: 10
tagggtctag aaataatttt gtttaacttt aagaaggaga tataccatga cgaacgaacc   60
ggacc                                                              65

<210> SEQ ID NO 11
<211> LENGTH: 56
<212> TYPE: DNA
<213> ORGANISM: Artificial sequence
<220> FEATURE:
<223> OTHER INFORMATION: synthesized

<400> SEQUENCE: 11
agacccgttt agaggcccca aggggttatg ctagttattc gaacagactg cggatg       56

<210> SEQ ID NO 12
<211> LENGTH: 56
<212> TYPE: DNA
<213> ORGANISM: Artificial sequence
<220> FEATURE:
<223> OTHER INFORMATION: Nucleotide sequence

<400> SEQUENCE: 12
agtcctaggt ataatactag ttaccgggca taccgatgcg agttttagag ctagaa       56

<210> SEQ ID NO 13
<211> LENGTH: 56
<212> TYPE: DNA
<213> ORGANISM: Artificial sequence
<220> FEATURE:
<223> OTHER INFORMATION: synthesized

<400> SEQUENCE: 13
ttctagctct aaaactcgca tcggtatgcc cggtaactag tattatacct aggact       56

<210> SEQ ID NO 14
<211> LENGTH: 20
<212> TYPE: DNA
<213> ORGANISM: Artificial sequence
<220> FEATURE:
<223> OTHER INFORMATION: synthesized

<400> SEQUENCE: 14
acccaacctt acgcaaccag                                              20

<210> SEQ ID NO 15
<211> LENGTH: 76
<212> TYPE: DNA
<213> ORGANISM: Artificial sequence
<220> FEATURE:
```

<223> OTHER INFORMATION: synthesized

<400> SEQUENCE: 15
aattgttatc cgctcacaat tccacacatt atacgagccg gatgattaat tgtcaattgt    60
tcgataaccg cagcat                                                    76

<210> SEQ ID NO 16
<211> LENGTH: 80
<212> TYPE: DNA
<213> ORGANISM: Artificial sequence
<220> FEATURE:
<223> OTHER INFORMATION: synthesized

<400> SEQUENCE: 16
aaagactggg cctttcgttt tatctgttgt ttgtcggtga acgctctcct gagtaggaca    60
aatcgctggc gtgctttgaa                                                80

<210> SEQ ID NO 17
<211> LENGTH: 19
<212> TYPE: DNA
<213> ORGANISM: Artificial sequence
<220> FEATURE:
<223> OTHER INFORMATION: synthesized

<400> SEQUENCE: 17
ggcgtaactc agcaggcag                                                 19

<210> SEQ ID NO 18
<211> LENGTH: 84
<212> TYPE: DNA
<213> ORGANISM: Artificial sequence
<220> FEATURE:
<223> OTHER INFORMATION: synthesized

<400> SEQUENCE: 18
tccggctcgt ataatgtgtg gaattgtgag cggataacaa tttcacacag gaaacagacc    60
atggctgata caaaagcaaa actc                                           84

<210> SEQ ID NO 19
<211> LENGTH: 88
<212> TYPE: DNA
<213> ORGANISM: Artificial sequence
<220> FEATURE:
<223> OTHER INFORMATION: synthesized

<400> SEQUENCE: 19
caccgacaaa caacagataa aacgaaaggc ccagtctttc gactgagcct ttcgttttat    60
ttgttaacgc ttgatatcgc ttttaaag                                       88

<210> SEQ ID NO 20
<211> LENGTH: 56
<212> TYPE: DNA
<213> ORGANISM: Artificial sequence
<220> FEATURE:
<223> OTHER INFORMATION: synthesized

<400> SEQUENCE: 20
agtcctaggt ataatactag tacactggct ggatgtgcaa cgttttagag ctagaa        56

<210> SEQ ID NO 21
<211> LENGTH: 56
<212> TYPE: DNA
<213> ORGANISM: Artificial sequence

```
<220> FEATURE:
<223> OTHER INFORMATION: synthesized

<400> SEQUENCE: 21
ttctagctct aaaacgttgc acatccagcc agtgtactag tattatacct aggact      56

<210> SEQ ID NO 22
<211> LENGTH: 21
<212> TYPE: DNA
<213> ORGANISM: Artificial sequence
<220> FEATURE:
<223> OTHER INFORMATION: synthesized

<400> SEQUENCE: 22
cgtggagttg aaggtgttgg t                                             21

<210> SEQ ID NO 23
<211> LENGTH: 41
<212> TYPE: DNA
<213> ORGANISM: Artificial sequence
<220> FEATURE:
<223> OTHER INFORMATION: synthesized

<400> SEQUENCE: 23
tccttcgccg ctttaatcac cggcaatcca ctccagtaat t                       41

<210> SEQ ID NO 24
<211> LENGTH: 41
<212> TYPE: DNA
<213> ORGANISM: Artificial sequence
<220> FEATURE:
<223> OTHER INFORMATION: synthesized

<400> SEQUENCE: 24
aattactgga gtggattgcc ggtgattaaa gcggcgaagg a                       41

<210> SEQ ID NO 25
<211> LENGTH: 20
<212> TYPE: DNA
<213> ORGANISM: Artificial sequence
<220> FEATURE:
<223> OTHER INFORMATION: synthesized

<400> SEQUENCE: 25
taatagaggc gtcgccagct                                               20

<210> SEQ ID NO 26
<211> LENGTH: 56
<212> TYPE: DNA
<213> ORGANISM: Artificial sequence
<220> FEATURE:
<223> OTHER INFORMATION: synthesized

<400> SEQUENCE: 26
agtcctaggt ataatactag tacggaactg gcgcaacaag cgttttagag ctagaa       56

<210> SEQ ID NO 27
<211> LENGTH: 56
<212> TYPE: DNA
<213> ORGANISM: Artificial sequence
<220> FEATURE:
<223> OTHER INFORMATION: synthesized

<400> SEQUENCE: 27
ttctagctct aaaacgcttg ttgcgccagt tccgtactag tattatacct aggact      56
```

<210> SEQ ID NO 28
<211> LENGTH: 21
<212> TYPE: DNA
<213> ORGANISM: Artificial sequence
<220> FEATURE:
<223> OTHER INFORMATION: synthesized

<400> SEQUENCE: 28
gagctggcgt agtcacggta a                                              21

<210> SEQ ID NO 29
<211> LENGTH: 42
<212> TYPE: DNA
<213> ORGANISM: Artificial sequence
<220> FEATURE:
<223> OTHER INFORMATION: synthesized

<400> SEQUENCE: 29
ttcgctggca atgactttca cagaagttta ttgcgttgtg gc                       42

<210> SEQ ID NO 30
<211> LENGTH: 42
<212> TYPE: DNA
<213> ORGANISM: Artificial sequence
<220> FEATURE:
<223> OTHER INFORMATION: synthesized

<400> SEQUENCE: 30
gccacaacgc aataaacttc tgtgaaagtc attgccagcg aa                       42

<210> SEQ ID NO 31
<211> LENGTH: 20
<212> TYPE: DNA
<213> ORGANISM: Artificial sequence
<220> FEATURE:
<223> OTHER INFORMATION: synthesized

<400> SEQUENCE: 31
gcacgacgga aggtgttgtt                                                20

<210> SEQ ID NO 32
<211> LENGTH: 56
<212> TYPE: DNA
<213> ORGANISM: Artificial sequence
<220> FEATURE:
<223> OTHER INFORMATION: synthesized

<400> SEQUENCE: 32
agtcctaggt ataatactag tccagctcaa gcccaatcca ggttttagag ctagaa        56

<210> SEQ ID NO 33
<211> LENGTH: 56
<212> TYPE: DNA
<213> ORGANISM: Artificial sequence
<220> FEATURE:
<223> OTHER INFORMATION: synthesized

<400> SEQUENCE: 33
ttctagctct aaaacctcgc ggccagatac gcatgactag tattatacct aggact        56

<210> SEQ ID NO 34
<211> LENGTH: 23
<212> TYPE: DNA
<213> ORGANISM: Artificial sequence
<220> FEATURE:
<223> OTHER INFORMATION: synthesized

<400> SEQUENCE: 34
ggtcaggagg taacttatca gcg                                              23

<210> SEQ ID NO 35
<211> LENGTH: 74
<212> TYPE: DNA
<213> ORGANISM: Artificial sequence
<220> FEATURE:
<223> OTHER INFORMATION: synthesized

<400> SEQUENCE: 35
aattgttatc cgctcacaat tccacacatt atacgagccg gatgattaat tgtcaaatgg      60
cagggctccg tttt                                                        74

<210> SEQ ID NO 36
<211> LENGTH: 88
<212> TYPE: DNA
<213> ORGANISM: Artificial sequence
<220> FEATURE:
<223> OTHER INFORMATION: synthesized

<400> SEQUENCE: 36
aaagactggg cctttcgttt tatctgttgt tgtcggtga acgctctcct gagtaggaca       60
aatgaactgg attttcttct gaacctgt                                         88

<210> SEQ ID NO 37
<211> LENGTH: 19
<212> TYPE: DNA
<213> ORGANISM: Artificial sequence
<220> FEATURE:
<223> OTHER INFORMATION: synthesized

<400> SEQUENCE: 37
acgatgtcag cagccagca                                                   19

<210> SEQ ID NO 38
<211> LENGTH: 84
<212> TYPE: DNA
<213> ORGANISM: Artificial sequence
<220> FEATURE:
<223> OTHER INFORMATION: synthesized

<400> SEQUENCE: 38
tccggctcgt ataatgtgtg gaattgtgag cggataacaa tttcacacag gaaacagacc      60
atgaaaaccc gtacacaaca aatt                                             84

<210> SEQ ID NO 39
<211> LENGTH: 86
<212> TYPE: DNA
<213> ORGANISM: Artificial sequence
<220> FEATURE:
<223> OTHER INFORMATION: synthesized

<400> SEQUENCE: 39
caccgacaaa caacagataa acgaaaggc ccagtctttc gactgagcct ttcgttttat       60
ttgttagaac tgcgattctt cagtgg                                           86

<210> SEQ ID NO 40
<211> LENGTH: 56
<212> TYPE: DNA
<213> ORGANISM: Artificial sequence
<220> FEATURE:

<223> OTHER INFORMATION: synthesized

<400> SEQUENCE: 40
agtcctaggt ataatactag tacagaatat tcgcgaaaaa agttttagag ctagaa        56

<210> SEQ ID NO 41
<211> LENGTH: 56
<212> TYPE: DNA
<213> ORGANISM: Artificial sequence
<220> FEATURE:
<223> OTHER INFORMATION: Nucleotide sequence

<400> SEQUENCE: 41
ttctagctct aaaactttt tcgcgaatat tctgtactag tattatacct aggact        56

<210> SEQ ID NO 42
<211> LENGTH: 20
<212> TYPE: DNA
<213> ORGANISM: Artificial sequence
<220> FEATURE:
<223> OTHER INFORMATION: synthesized

<400> SEQUENCE: 42
gtcaggcact ggcgaaagat        20

<210> SEQ ID NO 43
<211> LENGTH: 75
<212> TYPE: DNA
<213> ORGANISM: Artificial sequence
<220> FEATURE:
<223> OTHER INFORMATION: synthesized

<400> SEQUENCE: 43
aattgttatc cgctcacaat tccacacatt atacgagccg gatgattaat tgtcaacgca    60
agccataaac ccaca        75

<210> SEQ ID NO 44
<211> LENGTH: 77
<212> TYPE: DNA
<213> ORGANISM: Artificial sequence
<220> FEATURE:
<223> OTHER INFORMATION: synthesized

<400> SEQUENCE: 44
ctgggccttt cgttttatct gttgtttgtc ggtgaacgct ctcctgagta ggacaaattt    60
ccgacatcga aatgcgt        77

<210> SEQ ID NO 45
<211> LENGTH: 20
<212> TYPE: DNA
<213> ORGANISM: Artificial sequence
<220> FEATURE:
<223> OTHER INFORMATION: synthesized

<400> SEQUENCE: 45
aggcgttgtt gtggcagatt        20

<210> SEQ ID NO 46
<211> LENGTH: 81
<212> TYPE: DNA
<213> ORGANISM: Artificial sequence
<220> FEATURE:
<223> OTHER INFORMATION: synthesized

<400> SEQUENCE: 46

```
tccggctcgt ataatgtgtg gaattgtgag cggataacaa tttcacacag gaaacagacc    60
atgcgaattg gcataccaag a                                              81
```

<210> SEQ ID NO 47
<211> LENGTH: 82
<212> TYPE: DNA
<213> ORGANISM: Artificial sequence
<220> FEATURE:
<223> OTHER INFORMATION: synthesized

<400> SEQUENCE: 47

```
acaaacaaca gataaaacga aaggcccagt ctttcgactg agcctttcgt tttatttgtt    60
acagagcttt caggattgca tc                                             82
```

<210> SEQ ID NO 48
<211> LENGTH: 56
<212> TYPE: DNA
<213> ORGANISM: Artificial sequence
<220> FEATURE:
<223> OTHER INFORMATION: synthesized

<400> SEQUENCE: 48

```
agtcctaggt ataatactag tgctgaaaaa atatcgccca cgttttagag ctagaa        56
```

<210> SEQ ID NO 49
<211> LENGTH: 56
<212> TYPE: DNA
<213> ORGANISM: Artificial sequence
<220> FEATURE:
<223> OTHER INFORMATION: synthesized

<400> SEQUENCE: 49

```
ttctagctct aaaacgtggg cgatattttt tcagcactag tattatacct aggact        56
```

<210> SEQ ID NO 50
<211> LENGTH: 20
<212> TYPE: DNA
<213> ORGANISM: Artificial sequence
<220> FEATURE:
<223> OTHER INFORMATION: synthesized

<400> SEQUENCE: 50

```
tccttcagcc actcggacac                                                20
```

<210> SEQ ID NO 51
<211> LENGTH: 46
<212> TYPE: DNA
<213> ORGANISM: Artificial sequence
<220> FEATURE:
<223> OTHER INFORMATION: synthesized

<400> SEQUENCE: 51

```
gatagcagga atcctgatgc tttatggatg cgataatcgt caaaac                   46
```

<210> SEQ ID NO 52
<211> LENGTH: 46
<212> TYPE: DNA
<213> ORGANISM: Artificial sequence
<220> FEATURE:
<223> OTHER INFORMATION: synthesized

<400> SEQUENCE: 52

```
gttttgacga ttatcgcatc cataaagcat caggattcct gctatc                   46
```

<210> SEQ ID NO 53
<211> LENGTH: 24
<212> TYPE: DNA
<213> ORGANISM: Artificial sequence
<220> FEATURE:
<223> OTHER INFORMATION: synthesized

<400> SEQUENCE: 53
attatccgtt gcagttatga gtga                                          24

<210> SEQ ID NO 54
<211> LENGTH: 56
<212> TYPE: DNA
<213> ORGANISM: Artificial sequence
<220> FEATURE:
<223> OTHER INFORMATION: synthesized

<400> SEQUENCE: 54
agtcctaggt ataatactag tttgctcaga gtctgcaaac cgttttagag ctagaa       56

<210> SEQ ID NO 55
<211> LENGTH: 56
<212> TYPE: DNA
<213> ORGANISM: Artificial sequence
<220> FEATURE:
<223> OTHER INFORMATION: synthesized

<400> SEQUENCE: 55
ttctagctct aaaacggttt gcagactctg agcaaactag tattatacct aggact       56

<210> SEQ ID NO 56
<211> LENGTH: 20
<212> TYPE: DNA
<213> ORGANISM: Artificial sequence
<220> FEATURE:
<223> OTHER INFORMATION: synthesized

<400> SEQUENCE: 56
ttcatcggga cgagtggaga                                               20

<210> SEQ ID NO 57
<211> LENGTH: 76
<212> TYPE: DNA
<213> ORGANISM: Artificial sequence
<220> FEATURE:
<223> OTHER INFORMATION: synthesized

<400> SEQUENCE: 57
aattgttatc cgctcacaat tccacacatt atacgagccg gatgattaat tgtcaaccat   60
agcatcgcca atctga                                                   76

<210> SEQ ID NO 58
<211> LENGTH: 80
<212> TYPE: DNA
<213> ORGANISM: Artificial sequence
<220> FEATURE:
<223> OTHER INFORMATION: synthesized

<400> SEQUENCE: 58
ctgggccttt cgttttatct gttgtttgtc ggtgaacgct ctcctgagta ggacaaatac   60
ccaaaggtga agataaagcc                                               80

<210> SEQ ID NO 59
<211> LENGTH: 24

```
<212> TYPE: DNA
<213> ORGANISM: Artificial sequence
<220> FEATURE:
<223> OTHER INFORMATION: synthesized

<400> SEQUENCE: 59
cattccctct acagaactag ccct                                          24

<210> SEQ ID NO 60
<211> LENGTH: 82
<212> TYPE: DNA
<213> ORGANISM: Artificial sequence
<220> FEATURE:
<223> OTHER INFORMATION: synthesized

<400> SEQUENCE: 60
tccggctcgt ataatgtgtg gaattgtgag cggataacaa tttcacacag gaaacagacc   60
atgaacgaac aatattccgc at                                            82

<210> SEQ ID NO 61
<211> LENGTH: 80
<212> TYPE: DNA
<213> ORGANISM: Artificial sequence
<220> FEATURE:
<223> OTHER INFORMATION: synthesized

<400> SEQUENCE: 61
acaaacaaca gataaaacga aaggcccagt ctttcgactg agcctttcgt tttatttgtt   60
agccggtatt acgcatacct                                               80

<210> SEQ ID NO 62
<211> LENGTH: 56
<212> TYPE: DNA
<213> ORGANISM: Artificial sequence
<220> FEATURE:
<223> OTHER INFORMATION: synthesized

<400> SEQUENCE: 62
agtcctaggt ataatactag taacacagca atacggtacg cgttttagag ctagaa       56

<210> SEQ ID NO 63
<211> LENGTH: 56
<212> TYPE: DNA
<213> ORGANISM: Artificial sequence
<220> FEATURE:
<223> OTHER INFORMATION: synthesized

<400> SEQUENCE: 63
ttctagctct aaaacgcgta ccgtattgct gtgttactag tattatacct aggact       56

<210> SEQ ID NO 64
<211> LENGTH: 21
<212> TYPE: DNA
<213> ORGANISM: Artificial sequence
<220> FEATURE:
<223> OTHER INFORMATION: synthesized

<400> SEQUENCE: 64
actgacaact tcggcaccag a                                             21

<210> SEQ ID NO 65
<211> LENGTH: 44
<212> TYPE: DNA
<213> ORGANISM: Artificial sequence
<220> FEATURE:
```

```
<223> OTHER INFORMATION: synthesized

<400> SEQUENCE: 65
cagatgcggt gttagtagtg cctcttcaga ttcggttttc ggtc          44

<210> SEQ ID NO 66
<211> LENGTH: 44
<212> TYPE: DNA
<213> ORGANISM: Artificial sequence
<220> FEATURE:
<223> OTHER INFORMATION: synthesized

<400> SEQUENCE: 66
gaccgaaaac cgaatctgaa gaggcactac taacaccgca tctg          44

<210> SEQ ID NO 67
<211> LENGTH: 22
<212> TYPE: DNA
<213> ORGANISM: Artificial sequence
<220> FEATURE:
<223> OTHER INFORMATION: synthesized

<400> SEQUENCE: 67
aacctgccag cagagtagaa cc          22

<210> SEQ ID NO 68
<211> LENGTH: 56
<212> TYPE: DNA
<213> ORGANISM: Artificial sequence
<220> FEATURE:
<223> OTHER INFORMATION: synthesized

<400> SEQUENCE: 68
agtcctaggt ataatactag tcgcaacgtg atgagcaaaa cgttttagag ctagaa          56

<210> SEQ ID NO 69
<211> LENGTH: 56
<212> TYPE: DNA
<213> ORGANISM: Artificial sequence
<220> FEATURE:
<223> OTHER INFORMATION: synthesized

<400> SEQUENCE: 69
ttctagctct aaaacgtttt gctcatcacg ttgcgactag tattatacct aggact          56
```